United States Patent
Glazier

(10) Patent No.: US 7,229,475 B2
(45) Date of Patent: Jun. 12, 2007

(54) MULTI-FOCAL INTRAOCULAR LENS, AND METHODS FOR MAKING AND USING SAME

(75) Inventor: Alan Glazier, Rockville, MD (US)

(73) Assignee: Vision Solutions Technologies, Inc., Rockville, MD (US)

( * ) Notice: Subject to any disclaimer, the term of this patent is extended or adjusted under 35 U.S.C. 154(b) by 353 days.

(21) Appl. No.: 10/733,173

(22) Filed: Dec. 10, 2003

(65) Prior Publication Data

US 2005/0071002 A1  Mar. 31, 2005

Related U.S. Application Data

(63) Continuation-in-part of application No. PCT/US02/17964, filed on Jun. 7, 2002, which is a continuation-in-part of application No. 10/158,574, filed on May 30, 2002, now Pat. No. 6,855,164, which is a continuation-in-part of application No. 10/139,144, filed on May 3, 2002, now abandoned.

(60) Provisional application No. 60/297,306, filed on Jun. 11, 2001.

(51) Int. Cl.
*A61F 2/16* (2006.01)

(52) U.S. Cl. ..................... 623/6.13; 623/6.37

(58) Field of Classification Search ................. 623/4.1, 623/6.11, 6.13, 6.22, 6.23, 6.24, 6.27, 6.37, 623/6.56
See application file for complete search history.

(56) References Cited

U.S. PATENT DOCUMENTS

| | | | |
|---|---|---|---|
| 2,437,642 A | 3/1948 | Henroteau | |
| 2,714,721 A | 9/1955 | Stone | |
| 2,834,023 A | 5/1958 | Lieb | |
| 3,598,479 A | 8/1971 | Wright et al. | |
| 3,614,215 A | 10/1971 | Mackta | |
| 3,673,616 A | 7/1972 | Fedorov et al. | |
| 3,711,870 A | 1/1973 | Deitrick | |
| 3,866,249 A | 2/1975 | Flom | |
| 3,906,551 A | 9/1975 | Otter | |
| 3,913,148 A | 10/1975 | Potthast | |
| 4,010,496 A | 3/1977 | Neefe | |

(Continued)

FOREIGN PATENT DOCUMENTS

| | | |
|---|---|---|
| DE | 4340205 | 4/1995 |
| FR | 1279252 | 12/1961 |

*Primary Examiner*—William H Matthews
(74) *Attorney, Agent, or Firm*—Berenato, White & Stavish, LLC

(57) ABSTRACT

An intraocular lens is provided that includes an optic body having anterior and posterior walls, a chamber, and optically transmissive primary and secondary fluids, and method for making and using the same. The secondary fluid is substantially immiscible with the primary fluid and has a different density and a different refractive index than the primary fluid. The primary fluid is present in a sufficient amount that orienting optical body optical axis horizontally for far vision positions the optical axis through the primary fluid, thereby immersing the anterior and posterior optical centers in the primary fluid. The secondary fluid is contained in the optic body in a sufficient amount that orienting the optical axis over a range of effective downward angles relative to the horizontal for near vision positions the optical axis to extend through the primary fluid and the secondary fluid, thus changing the focus of the intraocular lens.

13 Claims, 16 Drawing Sheets

U.S. PATENT DOCUMENTS

| | | |
|---|---|---|
| 4,174,156 A | 11/1979 | Glorieux |
| 4,373,218 A | 2/1983 | Schachar |
| 4,477,158 A | 10/1984 | Pollock et al. |
| 4,512,040 A | 4/1985 | McClure |
| 4,636,211 A | 1/1987 | Nielsen et al. |
| 4,709,996 A | 12/1987 | Michelson |
| 4,710,193 A | 12/1987 | Volk |
| 4,720,286 A | 1/1988 | Bailey et al. |
| 4,731,079 A | 3/1988 | Stoy |
| 4,932,966 A | 6/1990 | Christie et al. |
| 4,994,058 A | 2/1991 | Raven et al. |
| 5,192,318 A | 3/1993 | Schneider et al. |
| 5,344,448 A | 9/1994 | Schneider et al. |
| 5,522,891 A | 6/1996 | Klaas |
| 5,628,798 A | 5/1997 | Eggleston et al. |
| 5,683,457 A | 11/1997 | Gupta et al. |
| 5,728,156 A | 3/1998 | Gupta et al. |
| 5,877,839 A | 3/1999 | Portney |
| 6,176,878 B1 | 1/2001 | Gwon et al. |
| 6,197,059 B1 | 3/2001 | Cumming |
| 6,210,438 B1 | 4/2001 | Sheets, Jr. et al. |
| 6,450,642 B1 | 9/2002 | Jethmalani et al. |
| 6,663,240 B2 | 12/2003 | Patel |
| 2002/0052652 A1 | 5/2002 | Schachar |
| 2003/0093149 A1 | 5/2003 | Glazier |
| 2003/0105522 A1 | 6/2003 | Glazier |
| 2003/0208267 A1 | 11/2003 | Buzard |

MULTI-FOCAL INTRAOCULAR LENS, AND METHODS FOR MAKING AND USING SAME

RELATED APPLICATIONS

This application is a continuation-in-part of PCT/US02/17964, filed Jun. 7, 2002, which is a continuation-in-part of U.S. patent application Ser. No. 10/158,574, filed in the U.S. Patent & Trademark Office on May 30, 2002, now U.S. Pat. No. 6,855,164 which is a continuation-in-part of U.S. patent application Ser. No. 10/139,144, filed in the U.S. Patent & Trademark Office on May 3, 2002, now abandoned the complete disclosures of which are incorporated herein by reference.

This application claims the benefit of priority of U.S. provisional patent application 60/297,306 filed in the U.S. Patent & Trademark Office on Jun. 11, 2001, the complete disclosure of which is incorporated herein by reference.

BACKGROUND OF THE INVENTION

1. Field of the Invention

This invention relates generally to bifocal and other multi-focal intraocular lenses, their production, and to their implantation and use in the eye. In particularly preferred embodiments, the invention relates to the use of intraocular lenses in aphakia, pseudophakia, anterior cortical cataract extraction (acce), posterior cortical cataract extraction (pcce), accommodative restorative surgery for presbyopes, treatment of retinal degenerative diseases (i.e., low vision) and in refractive correction surgery, and the like.

2. Description of Related Art

A general discussion of the human eye physiology will be provided for the purpose of furthering an understanding of this invention. Generally, the most outwardly visible structures of the human eye include an optically clear anterior cornea, the iris sphincter sitting behind the cornea, and the aperture of the iris, which aperture is referred to as the pupil. The pupil usually appears as a circular opening concentrically inward of the iris. Light passes through the pupil along a path to the retina in the back of the eye. In a healthy human eye, a physiological crystalline lens with a capsular bag is positioned posterior to the iris. The chamber between the posterior cornea and the front surface of the capsular bag is commonly referred to in the art as the anterior chamber. A posterior chamber is the area behind the anterior chamber, and includes the capsular bag and physiological crystalline lens.

Ciliary muscle concentrically surrounds the capsular bag, and is coupled to the physiological crystalline lens by suspensory ligaments, also known as zonules. Vitreous humor is contained in the posterior chamber behind the capsular bag. The vitreous humor is surrounded by the retina, which is surrounded by the sclera. The functions and interrelationship of these structures of the human eye are well known in the art and, for this reason, are not elaborated upon in detail herein, except as is needed or useful for facilitating an understanding of this invention.

Light entering the emmetropic human eye is converged towards a point focus on the retina at a point known as the fovea. The cornea and tear film are responsible for the initial convergence of entering light. Subsequent to refraction by the cornea, the light passes through the physiological crystalline lens, where the light is refracted again. When focusing on an object, ideally the physiological crystalline lens refracts incoming light towards a point image on the fovea of the retina. The amount of bending to which the light is subjected is termed the refractive power. The refractive power needed to focus on an object depends upon how far away the object is from the principle planes of the eye. More refractive power is required for converging light rays to view close objects clearly than is required for converging light rays to view distant objects clearly.

A young and healthy physiological lens of the human eye has sufficient elasticity to provide the eye with natural accommodation ability. A young elastic lens may alter its shape, by a process known as accommodation, to change refractive power. The term accommodation refers to the ability of the eye to adjust focus between the distant point of focus, called the Punctum Remotum or pr (far point beyond 20 feet or 6 meters away), and the near point of focus called the Punctum Proximum or pp (near point within 20 feet or 6 meters away from the eye). Focus adjustment is performed in a young elastic lens using the accommodative-convergence mechanism. The ciliary muscle functions to shape the curvature of the physiological crystalline lens to an appropriate optical configuration for focusing light rays entering the eye and converging the light on the fovea of the retina. It is widely believed that this accommodation is accomplished via contracting and relaxing the ciliary muscle, which accommodate the lens of the eye for near and distant vision, respectively.

More specifically, the eye is "unaccommodated" for far vision by the ciliary muscle relaxing to decrease the convexity of the lens, according to accepted theoretical models of the function of the accommodative mechanism. In this unaccommodated state, the ciliary muscle relaxes, the suspensory zonules holding the lens in place and anchoring it to the ciliary muscle are at their greatest tension. The tension of the zonules causes the lens surfaces to take their flattest curves, making the retina conjugate with the far point pr. On the other hand, the ciliary muscle actively accommodates the eye for near vision by increasing the convexity of the lens within the eye via contraction of the muscle. In the accommodated state, the ciliary muscle is constricted in a sphincter-like mode, relaxing the zonules and allowing the lens to take a more convex form. In the fully accommodated state, the retina is coincident with the near point of accommodation pp. The maximum accommodative effort is termed the amplitude.

The term emmetropia is understood in the art to mean that natural focus of the optics of the eye when viewing a distant object (greater than 6 meters) is coincident with the retina. The term ammetropia means that the distance focus is displaced from the retina, such as in the case of hypermetropia, astigmatism, and myopia. Hypermetropia denotes an error of refraction caused when the retina intercepts the rays (or pencils) received by the eye before the rays reach their focus. Myopia denotes an error of refraction caused when the pencils within the eye focus to a real point before the pencils reach the retina.

According to one theory, the physiological crystalline lens slowly loses its elasticity as it ages. As the physiological crystalline lens ages, the alteration in curvature becomes less for the same action of the ciliary muscle. According to another theory, the physiological lens enlarges with age causing a decrease in working distance between the ciliary body and the lens, resulting in decreased focus ability for the same muscle action. For most people, generally the decline in focusing ability starts in youth and continues until the age of about 60. Generally, it becomes necessary for most people around the age of 40 to use near addition lenses to artificially regain sufficient amplitude at near to accommodate for the pp when attempting to perform near-point activities such as reading. This condition is known as presbyopia, and afflicts or will afflict almost every human being.

With presbyopia, incoming light rays from the pp are focused at a virtual point situated behind the retina. The ciliary body-zonules-lens complex becomes less efficient at accommodating the focus of these rays on the retina. Convergence of the rays in a healthy, phakic (with lens) eye having presbyopia is most commonly achieved with the assistance of eyeglass lenses, contact lenses, or refractive surgery. Distance and near objects can then be seen clearly.

Aphakia is the condition in which the crystalline lens is either absent or, in very rare cases, displaced from the pupillary area so that it adversely affects the eye's optical focusing system. The former condition may be congenital, but it is usually the result of cataract-removal surgery. With advancing age, the physiological crystalline lens tends to develop opacities—a condition known as cataractogenesis—which unless treated eventually leads to blindness.

In the absence of other pathology or degenerative changes, removal of the opaque crystalline lens afflicted with cataracts restores the possibility of obtaining good vision with refractive implements such as eyeglasses, contact lenses, or intraocular lenses. Pseudophakia occurs when the crystalline lens is replaced with a synthetic intraocular lens.

Removal of the crystalline lens by surgery entails the loss of ability to accommodate, so additional positive power in the form of a near addition is needed for near focus. If the synthetic lens is of proper power and results in the pr focusing on the retina, the refractive error for distance will have been eliminated. However, current synthetic intraocular lenses lack the flexibility of a physiological crystalline lens. As a consequence, it is difficult, if not impossible, for the ciliary muscle to focus current synthetic intraocular lenses in the same way as a physiological lens to adjust for objects near the pp. Thus, conventional monofocal intraocular lenses provide little, if any accommodating ability.

Generally, a plus-powered eyeglass lens or contact lens is used in conjunction with an eye having a synthetic intraocular lens to adjust for objects near the pp. Pseudophakic individuals corrected for distance and emmetropia will usually require a lens in front of their eye the equivalent of approximately +2.50 diopters of power to be able to focus on near-point objects between 12 and 20 inches from the eye (approximate). However, "reading" glasses and contact lenses have the drawbacks of being inconvenient, uncomfortable, susceptible to loss and breakage, and in the case of glasses, aesthetically undesirable to some users.

Several synthetic intraocular lenses exist with zones that alter near focus powers with distance, claiming to assist the pseudophake with viewing near objects. An example of such an intraocular lens is U.S. Pat. No. 5,344,448. One problem with these designs is the zones of far and near are present simultaneously on the retina, thereby resulting in some blur or visual distortion at distance and near.

An intraocular lens that uses multiple fluids of different refractive indices is disclosed in U.S. Pat. No. 4,720,286. The intraocular lens of the '286 patent is comprised of a solid transmissive material having a hollow lenticule that encompasses the optical zone of the eye. By moving fluids of different indices of refraction through the lenticule, the lens can be made to change its power.

The inventor is unaware of any existing intraocular lens capable of effectively and actively altering focus from distance to near and back in presbyopic or pseudophakic individuals by utilizing the natural movement of the human eye and/or head. Attempts to create a "focusing" intraocular synthetic lens have been less than successful, and presbyopia, whether age-related or in pseudophakia, continues to be a vexing problem within eye care with no highly successful solutions yet in existence.

Another drawback to intraocular lenses is that an eye that has received an implant for restoring the natural accommodation of the eye may have its refractive error changed by the process of the implantation itself. In this event, the focusable implant may function properly, but the powers needed to achieve clear distance focus may not be the same as calculated prior to insertion of the implant. For example, an IOL selected for an eye of a particular length that is to be operated on might not function to fully correct maximum distance vision after the eye has healed. As the eye heals, the lens may settle off-axis, tilt, or translate further forward or backward than the surgeon intended, leaving a refractive error that will make it necessary for the patient to use distance corrective lenses to see clearly.

Another condition that afflicts many persons is retinal degenerative disease, specifically that in which a person's central vision is slowly destroyed, leaving the person with a "scotoma" or blurred out spot in their vision. This is most applicable to macular degeneration, but may occur as a result of most if not all retinal degenerative conditions (RDC's). An example that applies to the distance vision would be a person trying to discern the details of another person's face that is at a distance from them. For example, the person with a RDC may be able to tell where the viewed person's head is and see the body, but facial details appear "wiped-out" with a retinal degenerative condition that affects the macula.

The person who suffers from RDC's is typically treated optically by using magnification in lens form. At distance, a Galilean telescopic magnifying device may be placed in front of the eye or in the eye and customized to the user's needs. The magnification of the device enlarges the image viewed, expanding the image into more healthy areas of retina peripheral to the scotoma, effectively shrinking the scotoma for the user and allowing the user to better discern the image. At near, the person suffering from RDC's usually needs magnification in the form of magnifying plus powered lenses and/or prisms—the former (i.e., the plus lenses and magnifiers) to help enlarge the image outside of the scotoma as in the telescopic example and the latter (e.g., the prisms) to help shift the images to different, healthier areas of the retina.

Devices used to provide magnification at distance and near are prescribed according to the art and science of "low-vision." An example of a low vision device for distance use is a spectacle-mounted telescopic device. An example of a low vision device for near use is a hand-held magnification device and/or prism to assist the user in seeing peripheral to the damaged area of the retina, or scotoma. Devices used to provide magnification at distance and near have several drawbacks. First of all, the devices are heavy and bulky making them difficult to use from an ergonomic perspective. Second, the devices, such as those mounted on a pair of spectacles, may be considered aesthetically unappealing by some. Third, the devices may distort or decrease the effectiveness of magnification, for example, in the case of spectacle-mounted telescopic devices in which there exists a vertex distance (the distance from the back of the lens to the front of the cornea). Fourth, the devices limit the user's mobility as the telescopic devices are usually housed in a casing that limits the user's peripheral vision. Fifth, in the example of near vision magnification, the devices are often housed in a hand held device, which requires the user to not have "hands free" use of the device, i.e., the user may have trouble holding a newspaper in one hand and a device in the other. Sixth, current implantable telescope lenses are held within bulky housings, which decrease the user's peripheral vision and result in a significant decrease in the user's mobility.

Objects of the Invention

An object of this invention is to provide an intraocular lens ("IOL") that overcomes the above-described problems associated with the related art and restores a focus mechanism in presbyopic and pseudophakic eyes by providing accommodative function, with the shift from far to near vision and near to far vision by natural tilting movement of the head and/or eye, smoothly and without significant disruption to the field of vision.

Another object of this invention is to provide a method by which the intraocular lens of this invention may be implanted and used in a human eye to replace or supplement a physiological or synthetic lens.

Another object of this invention involves the treatment of one or more residual refractive disorders of the eye after the eye has received an element that allows it to focus, e.g., a multi-focal intraocular lens or other element that is designed to substitute for or increase the function of the human accommodative system.

Another object of this invention involves the treatment of retinal degenerative disorders with an accommodative multi-focal intraocular lens.

Additional objects and advantages of the invention will be set forth in the description that follows, and in part will be apparent from the description, or may be learned by practice of the invention. The objects and advantages of the invention may be realized and obtained by means of the instrumentalities and combinations pointed out in the appended claims.

SUMMARY OF THE INVENTION

To achieve one or more of the foregoing objects, and in accordance with the purposes of the invention as embodied and broadly described in this document, an intraocular lens of a first aspect of this invention comprises an optic body receivable into the human eye. The optic body comprises an anterior wall with an anterior optical center, a posterior wall with a posterior optical center, and a chamber between the anterior wall and the posterior wall. The optic body has an optical axis intersecting the anterior wall at the anterior optical center and the posterior wall at the posterior optical center. The intraocular lens of this first aspect of the invention also comprises optically transmissive primary and secondary fluids. The primary fluid has a first density and a first refractive index, and is contained in the chamber of the optic body in a sufficient amount that orienting the optical axis in a horizontal orientation for far vision positions the optical axis through the primary fluid, but not the secondary fluid. The anterior and posterior optical centers are thereby immersed in the primary fluid. The secondary fluid is substantially immiscible with the primary fluid and has a second density and a second refractive index that are different than the first density and the first refractive index of the primary fluid. The secondary fluid is contained in the chamber of the optic body in a sufficient amount that orienting the optical axis at a range of effective downward angles (so that the anterior wall faces downward in a downgaze) relative to the horizontal orientation for near vision positions the optical axis to extend through the primary fluid and the secondary fluid. Because the optical axis passes through both the first and second fluids in the downward gaze, a different total refractive index is established compared to the refractive index for the straight-ahead gaze. In a first preferred embodiment, the primary fluid has a greater density than the secondary fluid, and orienting the optical axis at a range of the effective downward angles translates the primary fluid toward the anterior wall and positions the optical axis to extend through the primary fluid at the anterior optical center and the secondary fluid at the posterior optical center. In a second preferred embodiment, the secondary fluid has a greater density than the primary fluid, and orienting the optical axis at the range of effective downward angles translates the secondary fluid toward the anterior wall and positions the optical axis to extend through the secondary fluid at the anterior optical center and the primary fluid at the posterior optical center.

According to an embodiment of the first aspect of the invention, the primary fluid comprises an optically transmissive lower liquid, and is contained in the chamber of the optic body in a sufficient amount that orienting the optical axis in a horizontal orientation for far vision positions the optical axis through the lower liquid for immersing most of the anterior surface area of the anterior visual zone and most of the posterior surface area of the posterior visual zone in the lower liquid. The secondary fluid comprises an optically transmissive upper fluid substantially immiscible with the lower liquid, and is contained in the chamber of the optic body above the lower liquid in a sufficient amount that orienting the optical axis for near vision at a range of effective downward angles relative to the horizontal orientation translates the lower liquid toward the anterior wall and positions the optical axis to extend through the lower liquid at the anterior optical center and the upper fluid at the posterior optical center for immersing most of the anterior surface area of the anterior visual zone with the lower liquid and most of the posterior surface area of the posterior visual zone in the upper fluid.

According to another embodiment of the first aspect of the invention, the primary fluid comprises an optically transmissive upper fluid, and is contained in the chamber of the optic body in a sufficient amount that orienting the optical axis in a horizontal orientation for far vision positions the optical axis through the upper fluid for immersing most of the anterior surface area of the anterior visual zone and most of the posterior surface area of the posterior visual zone in the upper fluid. Further, the secondary fluid comprises an optically transmissive lower liquid substantially immiscible with the upper fluid, and is contained in the chamber of the optic body below the upper fluid in a sufficient amount that orienting the optical axis for near vision at a range of effective downward angles relative to the horizontal orientation for near vision translates the lower liquid toward the anterior wall and positions the optical axis to extend through the lower liquid at the anterior optical center and the upper fluid at the posterior optical center for immersing most of the anterior surface area of the anterior visual zone with the lower liquid and most of the posterior surface area of the posterior visual zone in the upper fluid.

In accordance with the construction of the intraocular lens of this invention, multi-focus vision is achieved by the natural motion of the user's eye and/or head, preferably without requiring external visual correction devices, such as eyeglasses or contact lenses. For distant or far vision, the user gazes straight ahead to orient the optical axis substantially parallel to the horizon. In this straight-ahead gaze, the optical axis passes through either the optically transmissive lower liquid or the optically transmissive upper fluid. The refractive index of the fluid through which the optical axis passes and the curvature of the optic body alter the effective power of the lens for focusing for far distance (at the pr).

As the natural inclination to view near objects causes the eye to angle downward for near vision, such as in the case for reading, the upper fluid and the lower liquid move relative to the lens body to pass the optical axis (and visual axis) through both the upper fluid and the lower liquid. The combined refractive indexes of the upper fluid and lower liquid and the curvature of the optic body alter the effective power of the lens for focusing for near objects (at the pp). Thus, as the eye and/or head tilts downward for reading, the position of the eye and the angle of the optical axis of the intraocular lens relative to the horizon changes. This tilting movement alters the power of the lens by intercepting the upper and lower fluids with the optical axis. The effective power of the lens is returned to normal as the optical axis returns to the horizontal orientation and one of the fluids is removed from interception with the optical axis.

In a preferred embodiment of this invention, the intraocular lens is elastically deformable, such as by folding, to facilitate its insertion into the eye. By elastically, it is meant that the lens has sufficient memory to return to its original shape.

In another preferred embodiment of this invention, the adjustment in effective power of the lens is achieved without any moving parts (other than the flow of the refractive liquids) and without requiring the division of the intraocular lens into separate compartments via internal channels that prevent or inhibit elastic deformation of the lens.

In a variant to the above-described aspect and embodiments of the invention, the optic body is designed to maintain distant vision when the head or eye is tilted above horizontal, i.e., when the user looks upward. In this preferred embodiment, the chamber of the optic body preferably includes a dike for inhibiting flow of the secondary fluid to the anterior and posterior optical centers when the optic body is oriented to angle the optical axis upward relative to the horizontal orientation. The dike may be formed, for example, in the anterior wall and/or the posterior wall of the optic body. It is especially preferred, but optional, for the dike to have sufficient dimension to prevent all of the secondary fluid from reaching the anterior and posterior visual zones when the optic body is oriented to place the optical axis upward and perpendicular to the horizontal orientation. The dike is preferably in the form of a channel or protuberance, although this preferred embodiment is not necessarily limited to these physical structures. The dike is preferably in close proximity to the perimeter of the optic body, so that it is substantially outside the field of vision. The dike may undertake various shapes and patterns, including arcuate or annular shape formed about a portion or the entire optic body perimeter.

In accordance with another aspect of this invention, a method is provided for using the intraocular lens of this invention. According to one preferred embodiment, an incision is created in the cornea, conjunctiva, and/or sclera of an eye having a posterior chamber and an anterior chamber. The intraocular lens is inserted into either the anterior chamber or posterior chamber of the eye through the incision. Preferably, the intraocular lens is placed in the posterior chamber of the eye, and more preferably the intraocular lens replaces a disposable lens in the capsular bag positioned posterior to the iris. The methods of this invention are especially useful for replacing a physiological lens that is partially or virtually totally defective, such as in the case of low vision and/or a cataractous lens. The methods of this invention also find utility in the replacement or supplementation of partially defective lenses, in addition to providing low vision for macular degeneration, aiding myopia and hyperopia and presbyopia, where glasses, contact lenses, or other corrective devices are needed for correcting the partial defect. The lens may also be used in a refractive correction and/or presbyopic surgical procedure.

A method according to another aspect of this invention comprises optically moving images away from a scotomatous area of a person having a retinal degenerative condition. The method comprises inserting an ocular lens into an eye of the person having the retinal degenerative condition, the ocular lens comprising an optic body, an optically transmissive primary fluid, and an optically transmissive secondary fluid. The optical body comprises an anterior wall, a posterior wall, and a chamber between the anterior wall and the posterior wall, the optically transmissive primary and secondary fluids contained in the chamber and having different densities and refractive indexes from one another. The ocular lens preferably is designed so that orienting the human eye in a generally straight ahead gaze for far vision passes the visual axis through the primary liquid, but not the secondary liquid, for focusing on a distant point, and moving the human eye into a downward gaze to pass the visual axis through the primary liquid and the secondary liquid for focusing on a near point. The method preferably further comprises providing an objective lens in front of the ocular lens. Preferably, the ocular lens is negative in power in straight ahead gaze and more positive or more negative in power in down gaze relative to straight ahead gaze, and the objective lens has a positive power. Collectively, the ocular and objective lenses provide a Galilean telescopic effect in straight ahead gaze and increased magnification in down gaze.

In accordance with yet another aspect of this invention, a method is provided for making an intraocular lens for a human eye. The method of this aspect comprises forming an optic body sized and configured to be received in the human eye. This forming step may be performed by, for example, molding (e.g., injection molding) or lathing. The optic body comprises an anterior wall with an anterior optical center, a posterior wall with a posterior optical center, a chamber between the anterior wall and the posterior wall, and an entry port communicating with the chamber. An optical axis intersects the anterior wall at the anterior optical center and the posterior wall at the posterior optical center. Optically transmissive primary and secondary fluids are introduced, either together or consecutively, through the entry port and into the chamber of the optic body. The primary fluid has a first density and a first refractive index, and is contained in the chamber of the optic body in a sufficient amount that orienting the optical axis in a horizontal orientation for far vision positions the optical axis through the primary fluid and immerses the anterior and posterior optical centers in the primary fluid. The secondary fluid is substantially immiscible with the primary fluid, and has a second density and a second refractive index that are different than the first density and the first refractive index. The secondary fluid is contained in the chamber of the optic body in a sufficient amount that orienting the optical axis for near vision at a range of effective downward angles relative to the horizontal orientation positions the optical axis to extend through the primary fluid and the secondary fluid. After the primary and secondary fluids are introduced into the chamber, the entry port is closed to enclose the chamber.

The primary fluid and the secondary fluid used in this method may comprise a first liquid and a second liquid, respectively. A contact interface may be interposed between the first liquid and the second liquid, so that orienting the optical axis for near vision at a range of effective downward angles relative to the horizontal orientation positions the optical axis to extend through the contact interface. In one variation of this aspect, the first density is greater than the second density, and the primary liquid is introduced prior to the secondary fluid. Alternatively, the second density may be greater than the first density, and the secondary liquid may be introduced prior to the primary fluid.

In another modification to this aspect for making the intraocular lens, the optic body further comprises a vent. As the primary and secondary fluids are introduced through the entry port into the chamber, gas, if any, contained in the chamber is vented or expelled from the optic body through the vent.

It is to be understood that the aspects for using and making an intraocular lens, as described above, are not the exclusive methods that may be practiced with the intraocular lenses of this invention. Many variations, modifications, and alternative steps and methods to those described above may be used to make the intraocular lens of this invention.

In accordance with another aspect of this invention, there is provided a method for the treatment of one or more residual refractive disorders of the eye after the eye has received an element that allows it to focus, e.g., an intraocular lens or other element that is designed to substitute for or increase the function of the human accommodative system. In accordance with this aspect, an intraocular lens is implanted into the eye of a human being. After the eye has healed from the implantation surgery, residual refractive disorders of the eye are corrected by altering, e.g., reshaping, a structure of the eye, most preferably the cornea, to improve far distance vision. Sufficient healing to proceed with the altering step will usually take about 3 months, but may be longer or shorter depending upon the recuperative abilities of the eye and the successfulness of the implantation surgery. Preferably, but not necessarily, the intraocular lens of this aspect of the invention comprises a multi-focal intraocular lens of the one the aspects of the invention described herein. However, it is to be understood that this method may be employed with an accommodative intraocular lenses having conventional or other designs, as well as other intraocular devices that allow the eye to accommodate.

BRIEF DESCRIPTION OF THE DRAWINGS

The accompanying drawings are incorporated in and constitute a part of the specification. The drawings, together with the general description given above and the detailed description of the preferred embodiments and methods given below, serve to explain the principles of the invention. In the drawings.

Figure 1:
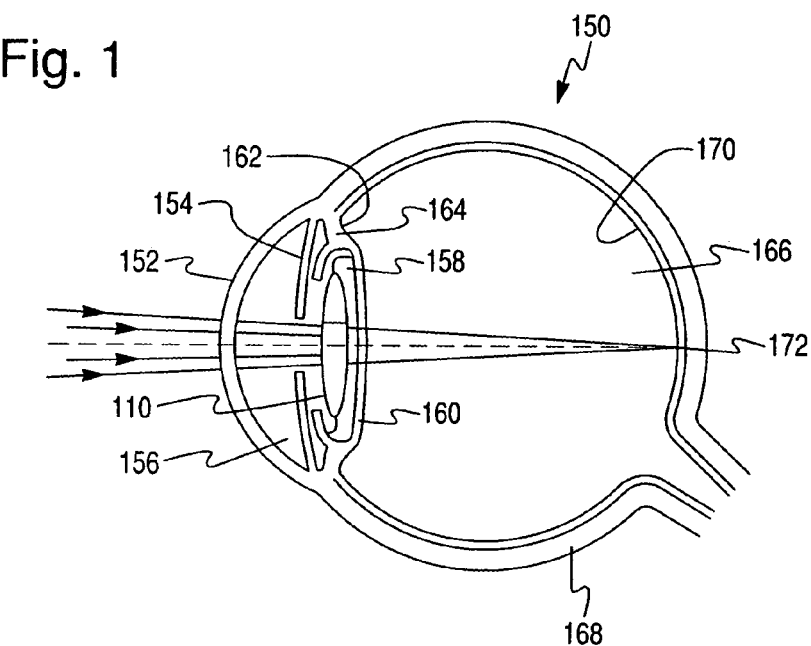
FIG. 1 is a schematic representation of a human eye with a posterior chamber containing an intraocular lens according to a first embodiment of the invention, in which the eye is gazing straight ahead at the horizon.

DETAILED DESCRIPTION OF THE PREFERRED EMBODIMENTS AND PREFERRED METHODS OF THE INVENTION

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

It is to be noted that, as used in the specification and the appended claims, the singular forms "a," "an," and "the" include plural referents unless the context clearly dictates otherwise.

FIGS. 1–4 illustrate an intraocular lens ("IOL"), generally designated by reference numeral 110, according to a first preferred embodiment of this invention. The intraocular lens comprises an optic body 112 sized and configured to be received in the capsular bag 160 of a human eye 150. The optic body 112 comprises an anterior wall 114, a posterior wall 116, and a chamber 118 between the anterior wall 114 and the posterior wall 116. The chamber 118 is preferably enclosed between the anterior wall 114 and the posterior wall 116, and more preferably is enclosed by a structure consisting of the anterior wall 114 and the posterior wall 116. The anterior and posterior walls 114 and 116 may be, for example, either made as a unitary "integral" piece or may be formed as separate members joined together to form the optic body 112. The optic body 112 has an optical axis 120 intersecting the anterior wall 114 at front vertex (apex) 114a and the posterior wall 116 at rear vertex (apex) 116a. The anterior wall 114 and posterior wall 116 are preferably spherical, although each may be aspheric, and may be modified into an aspheric shape or otherwise to compensate for astigmatism.

In the illustrated embodiment of FIGS. 1–4, the anterior wall 114 is convex and the posterior wall 116 is concave relative to the direction that light travels into the eye 150. However, it is to be understood that in this and other embodiments of the invention, the anterior wall 114 may be concave and/or the posterior wall 116 may be convex, depending upon the desired effective power and refractive properties of the lens 110. Thus, the optic body 112 may take on a convex-concave, convex-convex, concave-convex, or concave-concave configuration, depending upon the particular needs of the individual. Additionally, either the anterior wall 114 or the posterior wall 116 may have a non-curved or flat surface with a radius of curvature equal to zero. In the event one of the walls 114 or 116 is flat, its optical center is assumed to be a region directly opposing the optical center of the other wall.

Because the fluids possess refractive indices, it is possible for one of the walls 114 and 116 to possess no curvature, i.e., to be planar or non-curved. Further, the radii of curvature of the anterior wall 114 and the posterior wall 116 may have the same or different absolute values from each other, depending upon the desired strength of the lens 110. It is also within the scope of the invention to use multiple anterior walls 114 and/or multiple posterior walls 116, and/or to have the anterior wall 114 and/or posterior wall 116 comprised of laminates. Further, the anterior wall 114 and/or posterior wall 116 may be implanted with a lens element or bi-refringent materials. Another possibility is to employ anterior and/or posterior walls with discrete refractive zones, especially concentric zones, such as in the case of Fresnel magnification. However, the optic body 112 of this first embodiment and other embodiments described herein is preferably, although not necessarily, free of interior and exterior channels, especially those that would prevent the deforming or folding of the optic body 112.

An optically transmissive upper fluid 122 and an optically transmissive lower liquid 124 are contained in the chamber 118 of the optic body 112. It is preferred in this and other embodiments of the invention that the optically transmissive upper fluid 122 be a liquid, and that the liquids 122 and 124 fill the entire chamber 118, thereby eliminating any gases or free space within the chamber 118. The lower liquid 124 is denser than and has a different refractive index than the upper fluid 122. The upper fluid 122 and the lower liquid 124 are substantially immiscible with each other. As referred to herein, substantially immiscible means that the upper fluid and the lower liquid undergo no or sufficiently small amounts of intermixing that the function of the refractive fluids is performed, i.e., multi-focal sight is obtained by physical tilting of the intraocular lens.

Figure 2:
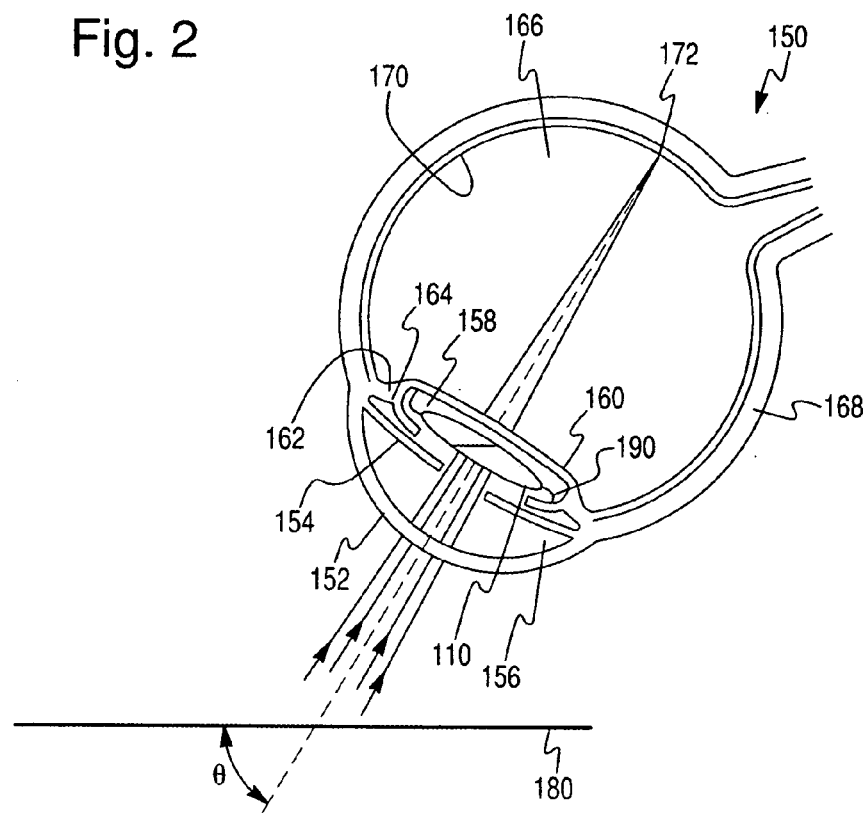
FIG. 2 is a schematic representation of the human eye containing the intraocular lens of FIG. 1, in which the eye is angled downward in a reading position.

A simplified schematic of the human eye having the intraocular lens 110 of this first embodiment implanted in its posterior chamber 158 of an eye 150 is illustrated in FIGS. 1 and 2. Referring to FIGS. 1 and 2, the eye 150 includes optically transmissive cornea 152, behind which is iris 154. The pupil (unnumbered) is interior to the iris 154 and commonly appears as a black circular area concentrically inward of the iris 154 when viewed from directly in front of the eye 150. The posterior chamber 158 of the eye 150 includes the capsular bag 160, which is shown in this embodiment holding the intraocular lens 110. The chamber between the cornea 152 and the front surface of the capsular bag 160, as shown in FIGS. 1 and 2, is commonly referred to in the art as anterior chamber 156.

Ciliary muscle 162 surrounds the capsular bag 160, and is coupled to the physiological crystalline lens (not shown) by zonules 164. The portion of the posterior chamber 158 behind the capsular bag 160 contains vitreous humor, which is interior to sclera 168. Coating the sclera is the conjunctiva (not shown). Light entering the human eye is converged on the retina 170 at the macula 172, through the optics of the cornea 152 and the intraocular lens 110. As light rays pass through the lens 110, the light rays are bent or refracted to a point at the macula 172 of the retina 170 to provide a clear image. Other light rays that are incident on the retina 170 away from the macula 172 are also detected, usually as part of one's peripheral vision.

The optical axis 120 is situated in the optic body 112 for placement along a light path 121 that enters through and is initially refracted by the cornea 152, then passes through the pupil to the retina 170. An optically transmissive anterior visual zone 114b of the anterior wall 114 defines a surface area through which the light path intersects the anterior wall 114. An optically transmissive posterior visual zone 116b of the posterior wall 116 defines a surface area through which the light path intersects the posterior wall 116. Although the visual zones 114b and 116b may be coextensive with the outer perimeters of the anterior and posterior walls 114 and 116, the visual zones 114b and 116b are more typically smaller in diameter and concentric with the outer perimeters of the anterior and posterior walls 114 and 116. If the lens 110 is positioned in the posterior chamber 156, i.e., posterior to the iris, then incoming light traveling along the light path is refracted by the lens 110 subsequent to passing through the iris 154. Thus, when the lens 110 is in the posterior chamber 158, the iris 154 functions to filter or block a portion of the light that passes through the cornea 152. As referred to herein, the light path through a posterior chamber lens represents the portion of the light that enters through the tear film (not shown) and cornea 152, passes through the pupil and is refracted by the posterior chamber lens 110 to the retina 172. On the other hand, if the lens 110 is positioned in the anterior chamber 156, incoming light traveling along the light path is refracted by the lens 110 before the light passes through the pupil of the iris 154. When the lens is in the anterior chamber 110, the iris 154 serves to filter or block a portion of the light leaving the lens. As referred to herein, the light path through an anterior chamber lens represents the portion of the light that enters through the cornea 152, is refracted by the anterior chamber lens and then passes through the pupil to the retina 172.

Figure 3:
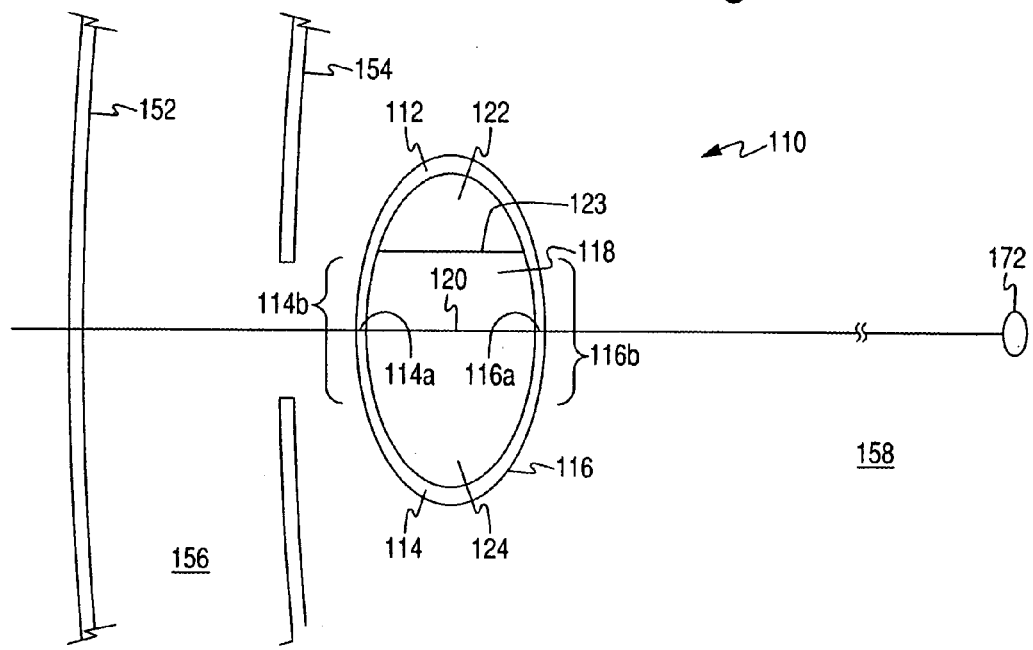
FIG. 3 is a schematic, enlarged view of the intraocular lens of FIGS. 1 and 2, depicting the lens oriented as shown in FIG. 1.
Figure 4:
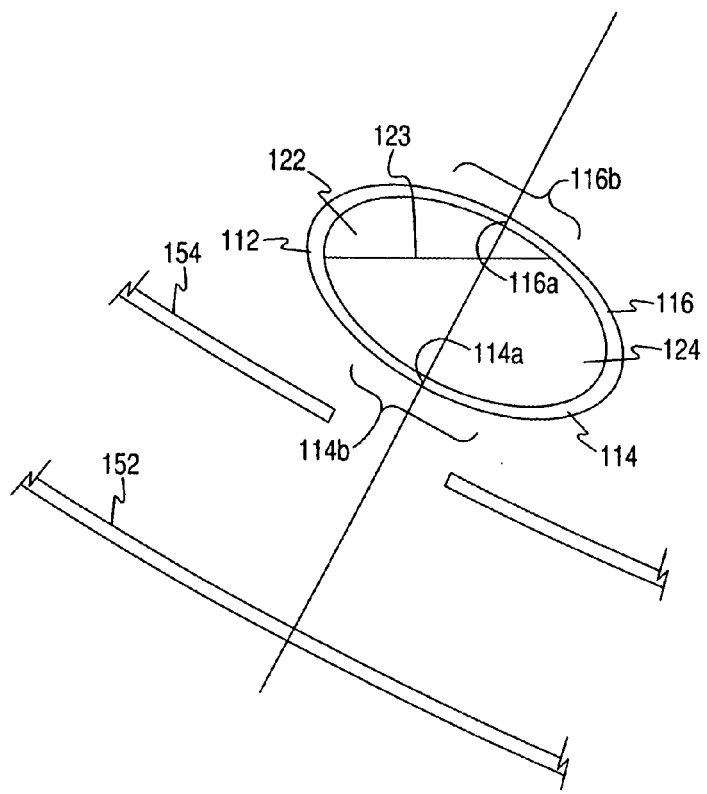
FIG. 4 is a schematic, enlarged view of the intraocular lens of FIGS. 1 and 2, depicting the lens oriented as shown in FIG. 2.

FIGS. 1 and 3 show the intraocular lens 110 of the first embodiment of this invention positioned in the posterior chamber 158 of the eye 150 gazing straight ahead at the pr. In this straight-ahead gaze, the optical axis 120 is parallel to the axis along the horizontal plane 180, or in a horizontal orientation. (Horizontal plane 180 is shown in FIG. 2. As is understood in the art, the eye is usually not rotationally symmetric, so that the optical axis and the visual axis are not co-linear. Hence, if the optical axis is horizontal, the visual axis is usually slightly offset from the horizon. For the purposes of this invention, the straight-ahead gaze refers to the position at which the optical axis is oriented horizontally.) The optically transmissive lower liquid 124 is present in a sufficient amount that orienting the optical axis 120 in the horizontal orientation for distant vision positions the optical axis 120 through the lower liquid 124, and most of the anterior visual zone 114b and the posterior visual zone 116b are immersed in the lower liquid 124. Because the anterior visual zone 114b and posterior visual zone 116b are typically substantially concentric about the front vertex 114a and the rear vertex 116a, contact interface 123 between the lower liquid 124 and the upper fluid 122 is above the vertexes 114a and 116a in the straight-ahead gaze. Preferably, the lower liquid 124 is present in a sufficient amount that in the straight-ahead gaze at least 70 percent, and more preferably all, of the anterior and posterior visual zones 114b and 116b are immersed in the lower liquid 124. Thus, in straight-ahead gaze, light entering the IOL travels along the optical axis and is primarily refracted by denser lower liquid 124. It is believed that any distortion caused by the presence of the fluid interface 123 (or plane of contact of the fluid 122 and liquid 124) in the anterior or posterior visual zone 114b or 116b will be minor and appear as glare to the extent it is even noticeable. The greater the portions of the visual zones 114b and 116b that are immersed in the lower liquid 124 in the straight-ahead gaze, the less the amount of glare or optical aberration, such as coma or halo, if any, that may occur.

The curvatures of the intraocular lens 110 are calculated to account for the refractive index of lower liquid 124 such that light travelling through the eye 150 from the Punctum Remotum may be focused on the macula 172. The anterior or posterior radii of curvature of the lens 110 may be selected depending upon the specific upper fluid 122 and lower liquid 124 chosen and the desired amount of accommodation. It is within the scope of the invention to form a lens which is capable of translating to any desired power for accommodation of eyesight, whether more (+) power or more (−) power upon down gaze. Adjustment of the lens power by modification of the optic body curvature is within the purview of those having ordinary skill in the art.

Figure 11:
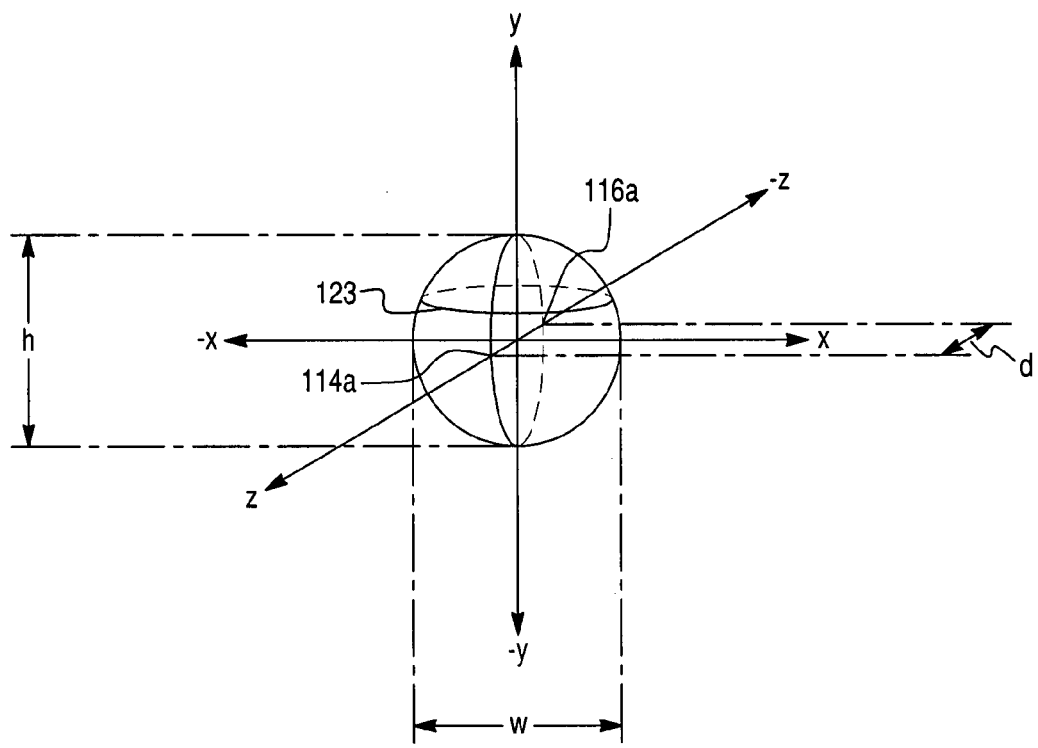
FIG. 11 is a simplified illustration of an intraocular lens optic body set on a Cartesian coordinate system.

On down gaze, the optical axis 120 rotates to an angle $\phi$ relative to the horizontal 180, as shown in FIG. 2. Referring now more particularly to FIG. 11, the lens body 112 is shown in a straight-ahead gaze centered on a Cartesian coordinate system. The lens body 112 has width (w), height (h), and depth (d) on the x, y, and z-axes, respectively. In FIG. 11, the optical axis 120, the front vertex 114a and the rear vertex 116a all rest on the z-axis. Generally, the down gaze involves displacement of the optical axis relative to the horizontal or z-axis by a range of effective angles $\phi$ to accomplish the objects of this invention. The effective angles $\phi$ may comprise angles throughout a range of 70–90 degrees, more preferably throughout a range of 45–90 degrees, and in some cases as large as angles throughout a range of 30–90 degrees. (Obviously, the natural tilting movement of the human head and/or eye does not pivot its intraocular lenses about a stationary x axis.)

In the down gaze, the optical axis 120 of this first embodiment is positioned at an angle $\phi$ relative to horizontal 180 to translate the lower liquid 124 higher on the anterior wall 114 and lower on the posterior wall 116. The upper fluid 122 is present in the chamber 118 in a sufficient amount that, at any effective angle $\phi$ within a range, the upper fluid 122 translates down the posterior wall 116 until the optical axis 120 extends through the upper fluid 122 at the back vertex 116a. Preferably, at the range of effective angles, most of the surface area of the anterior visual zone 114b is immersed in the lower liquid 124, and most of the posterior surface area of the posterior visual zone 116b is immersed in the upper fluid 122. More preferably, at the effective angles $\phi$ the anterior visual zone 114b has at least 70 percent of its surface area immersed in the lower liquid 124. As used herein, the term "most" may mean "all," in which case the anterior visual zone 114b has 100 percent of its surface area immersed in the lower liquid 124. (For the purposes of determining the percent immersed surface area, the anterior and posterior visual zones may be assumed to be those for an IOL of this invention implanted into an adult human emmetrope modeled as described in the Optical Society of America Handbook.) Simultaneously, at the effective angles $\phi$ the posterior visual zone 116b preferably has at least 70 percent of its surface area, and more preferably all (100 percent) of its surface area, immersed in the upper fluid 122. Under these conditions, the light rays first travels through the lower liquid 124, bathing the anterior visual zone 114b, before traveling through the contact interface 123 then the upper fluid 122 bathing the posterior visual zone 116b, before reaching the retina 170. Because the upper fluid 122 and the lower liquid 124 differ in refractive indices, light traveling through one medium will be refracted more than light traveling through the other medium.

In each of the embodiments described herein, it is preferred that the substantially immiscible fluids/liquids have a sufficiently low viscosity to permit them to freely translate at substantially the same time one's gaze changes from far-to-near and near-to-far. Thus, when the head or eye is returned to straight-ahead gaze, the fluids/liquids translate back to the primary position shown in FIGS. 1 and 3. For the first embodiment, the light rays that focus on the pr pass primarily through the lower liquid 124. This change in power is created without the need for convexity change (e.g., flexing) of the anterior surface 114 or posterior surface 116 of the optic body 112. The change in power is also accomplished without moving the lens 110 relative to the eye 150, i.e., towards or away from the macula 172. Thus, in the first embodiment, on down gaze the upper liquid 122 is translated into the visual axis to provide the desired amount of accommodation for near, and the lens adjusts back to distance focus as straight-ahead gaze is restored.

The range of effective angles $\phi$ at which the upper fluid 122 immerses a majority of the surface area of the posterior visual zone 116b is dependent upon the relative amounts of the upper fluid 122 and lower liquid 124 in the chamber 118. For this first embodiment in which the optical axis 120 passes through the lower liquid 124 in the straight ahead gaze (FIGS. 1 and 3), the higher the level of the lower liquid 124 in the chamber 118, the greater the angle $\phi$ to contact the upper fluid with the back vertex 116a. Other factors, such as lens thickness, lens radius, and volume shaping, may also affect the effective angle φ.

Referring back to FIG. 11, the width (w), height (h), and depth (d) of the lens body 112 will depend upon several factors, including the sizes of the patient's physiological lens, anterior chamber, and posterior chamber. Generally, the width (w) and height (h) of the lens body 112 may be, for example, in a range of 2.5 mm to 10 mm, more commonly 4.0 mm to 7.5 mm. The width (w) and height (h) are preferably, but not necessarily, the same in dimension. The depth (d) or thickness of the lens body 112 should not be so great as to inhibit implantation into the eye 150. On the other hand, the depth is preferably not so small that the anterior and posterior walls 114 and 116 create significant frictional influence to inhibit fluid translation in the chamber 118 of the lens body 112. The depth (d) may be, for example, at least 0.9 mm.

The anterior visual zone 114b and the posterior visual zone 116b are typically centered concentrically with the front vertex 114a and the rear vertex 116a. Typically, and for the purposes of this invention, the anterior visual zone 114b and the posterior visual zone 116b in an average human eye are about 2 mm to 7 mm in diameter, depending upon the size of the pupil.

Figure 7:
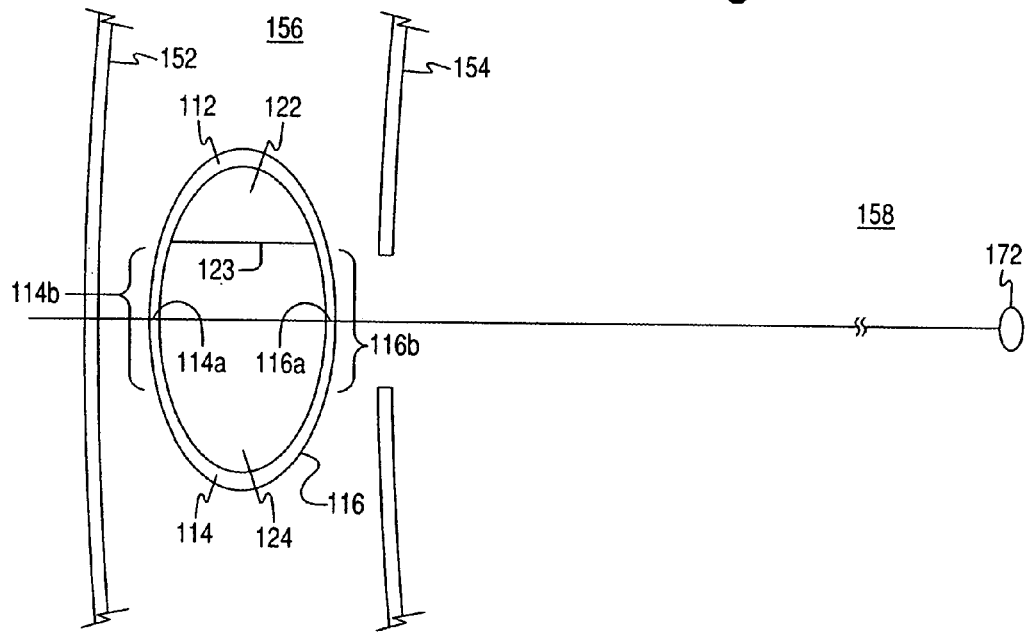
FIG. 7 is a schematic, enlarged view similar to FIG. 3, depicting the intraocular lens in the anterior chamber of the eye.
Figure 8:
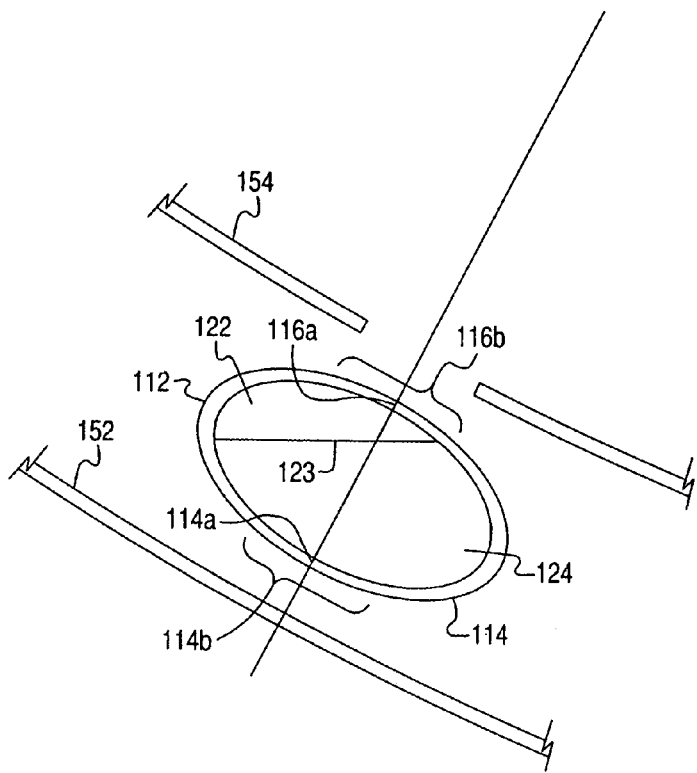
FIG. 8 is a schematic, enlarged view similar to FIG. 4, depicting the intraocular lens in the anterior chamber of the eye.

Although the intraocular lens of this first embodiment is illustrated in the posterior chamber 158 of the eye 150, it is to be understood that the lens 110 may be used in the anterior chamber 156, as shown in FIGS. 7 and 8. The intraocular lens 110 in the anterior chamber 156 may be the sole lens in the eye, or may supplement a physiological or synthetic lens placed in the posterior chamber 158. An anterior chamber implantation may be located in front of the iris 154 or between the iris 154 and the front surface of the capsular bag 160. The anterior chamber implantation may be anchored to the iris or in the angle recess.

Figure 5:
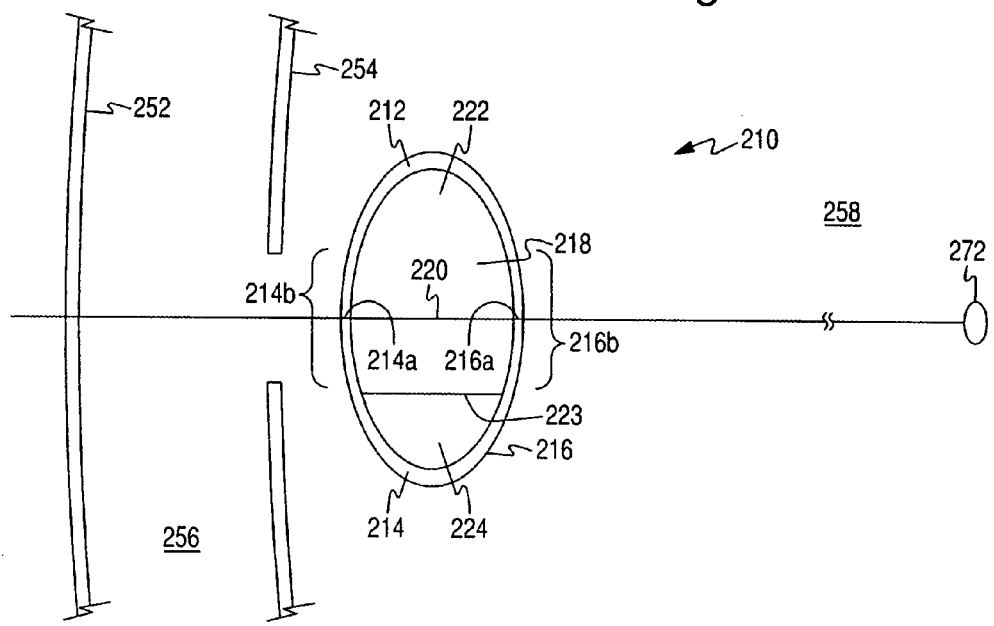
FIG. 5 is a schematic, enlarged view of an intraocular lens according to a second embodiment of this invention, depicting the lens in the posterior chamber of the eye oriented in a straight-ahead gaze.
Figure 6:
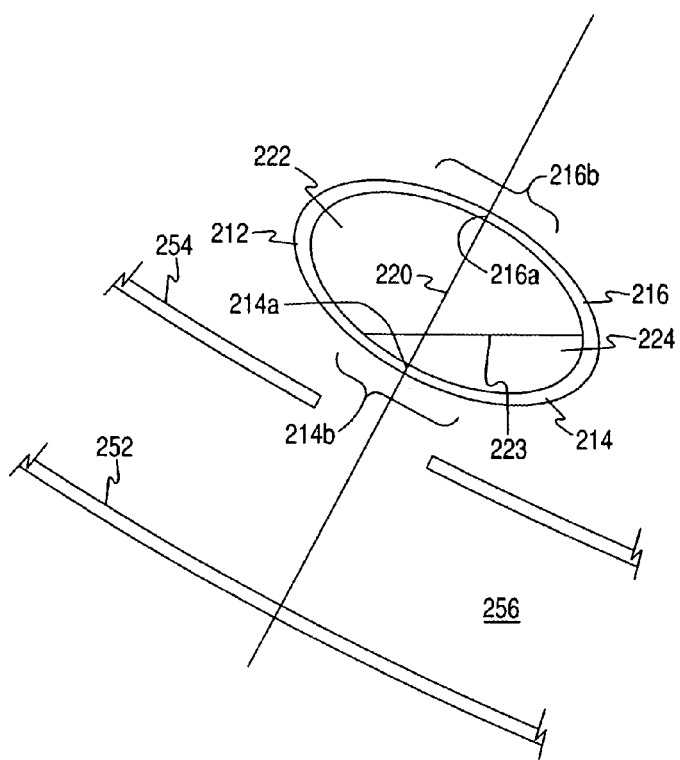
FIG. 6 is a schematic, enlarged view of the intraocular lens of the second embodiment of this invention, depicting the lens angled downward in a reading position.

An intraocular lens (IOL) 210 according to a second embodiment of this invention is illustrated in FIGS. 5 and 6. As with the first embodiment, the intraocular lens 210 of the second embodiment comprises an optic body 212 receivable in the capsular bag of a human eye. The optic body 212 comprises an anterior wall 214, a posterior wall 216, and a chamber 218 enclosed between the anterior wall 214 and the posterior wall 216. An optical axis 220 of the optic body 212 intersects the anterior wall 214 at a front vertex 214a and the posterior wall 216 at a rear vertex 216a.

As in the case of the first embodiment, in the second embodiment the intraocular lens 210 is designed for placement in the posterior chamber or anterior chamber of a human eye. The optical axis 220 is situated in the optic body 212 for placement in the human eye along a light path, which passes through the pupil to the retina 270. An optically transmissive anterior visual zone 214b of the anterior wall 214 defines a surface area through which the light path intersects the anterior wall 214. An optically transmissive posterior visual zone 216b of the posterior wall 216 defines a surface area through which the light path intersects the posterior wall 216.

FIG. 5 shows the intraocular lens 210 of the second embodiment of this invention positioned in the posterior chamber 258 of the eye gazing straight ahead at the pr. In this straight-ahead gaze, the optical axis 220 is parallel to the axis along the horizontal plane. The optically transmissive lower liquid 224 is present in a sufficient amount that orienting the optical axis 220 in a horizontal orientation positions the optical axis 220 through the upper fluid 222, and most of the anterior visual zone 214b and the posterior visual zone 216b are immersed in the upper fluid 222. Preferably, the upper fluid 222 is present in a sufficient amount that in the straight-ahead gaze at least 70 percent, and more preferably all, of the anterior and posterior visual zones 214b and 216b are immersed in the upper fluid 222. Thus, in straight-ahead gaze, light entering the IOL travels along the optical axis and is primarily refracted by the upper fluid 222. It is believed that any distortion caused by the presence of the fluid interface (i.e., plane of contact) 223 on the anterior or posterior visual zone 214b or 216b would be minor and appear as glare, to the extent it appears at all. The greater the portions of the visual zones 214b and 216b that are immersed in the upper fluid 222 in the straight-ahead gaze, the less the amount of glare or aberration, if any, that may occur.

The curvatures of the intraocular lens 210 are calculated to account for the refractive index of upper fluid 222 such that light travelling through the eye from the Punctum Remotum may be focused on the macula 272 of the eye. The anterior or posterior radii of curvature of the lens 210 may be selected depending upon the specific upper fluid 222 and lower liquid 224 chosen and the desired amount of accommodation. It is within the scope of the invention to form a lens which is capable of translating to any desired power for accommodation of eyesight, whether more (+) power or more (−) power upon down gaze.

On down gaze, the optical axis 220 rotates to an angle φ relative to the horizontal. As mentioned above, the down gaze generally involves displacement of the optical axis relative to the horizontal or z-axis by a range of effective angles φ to accomplish the objects of this invention. The effective angles φ may comprise a range of 70 to 90 degrees, more preferably 45 to 90 degrees, and in some cases over a range comprising 30 to 90 degrees.

In the down gaze, the optical axis 220 of this second embodiment is positioned at an angle φ relative to horizontal to translate the lower liquid 224 higher on the anterior wall 214 and lower on the posterior wall 216. The lower liquid 224 is present in the chamber 218 in a sufficient amount that, at the effective angles φ, the optical axis 220 extends through the lower liquid 224 at the front vertex 214a and the upper fluid 222 at the back vertex 216a. Preferably, in the down gaze most of the surface area of the anterior visual zone 214b is immersed in the lower liquid 224, and most of the surface area of the posterior visual zone 216b is immersed in the upper fluid 222. More preferably, at the effective angles φ (e.g., 70–90 degrees, 45–90 degrees, or 30–90 degrees), the anterior visual zone 214b has at least 70 percent of its surface area, and more preferably 100 percent of its surface area, immersed in the lower liquid 224. Simultaneously, at the effective angles φ the posterior visual zone 216b preferably has at least 70 percent of its surface area, and more preferably 100 percent of its surface area, immersed in the upper-fluid 222. Under these conditions, the light rays first travel through the lower liquid 224 bathing the anterior visual zone 214b before traveling through the contact interface 223 and the upper fluid 222 bathing the posterior visual zone 216b, before reaching the retina. Because the upper fluid 222 and the lower liquid 224 differ in refractive indices, light traveling through one medium will be refracted more than light traveling through the other medium.

The range of effective angles φ necessary for displacing the lower fluid 222 to contact the front vertex 214a is dependent upon the relative amounts of the upper fluid 222 and lower liquid 224 in the chamber 218. For this second embodiment in which the optical axis 220 passes through the upper fluid 222 in the straight ahead gaze (FIG. 5), lower levels of the lower liquid 224 generally will require greater effective angles φ for contacting the lower liquid 224 with the front vertex 214*a*. Preferably, however, a sufficient amount of the lower liquid 224 is present in this second embodiment that the bi-focal effect is realized throughout at least a range of effective angles of 70–90 degrees.

One particularly advantageous feature embodied in certain aspects of this invention is that orientation of the optical axis perpendicular to the horizon, so that the patient's head is directed straight downward, causes the optical axis to pass through both the upper fluid and the lower liquid, thereby accommodating for near-sight. This feature is especially useful for reading.

Figure 9:
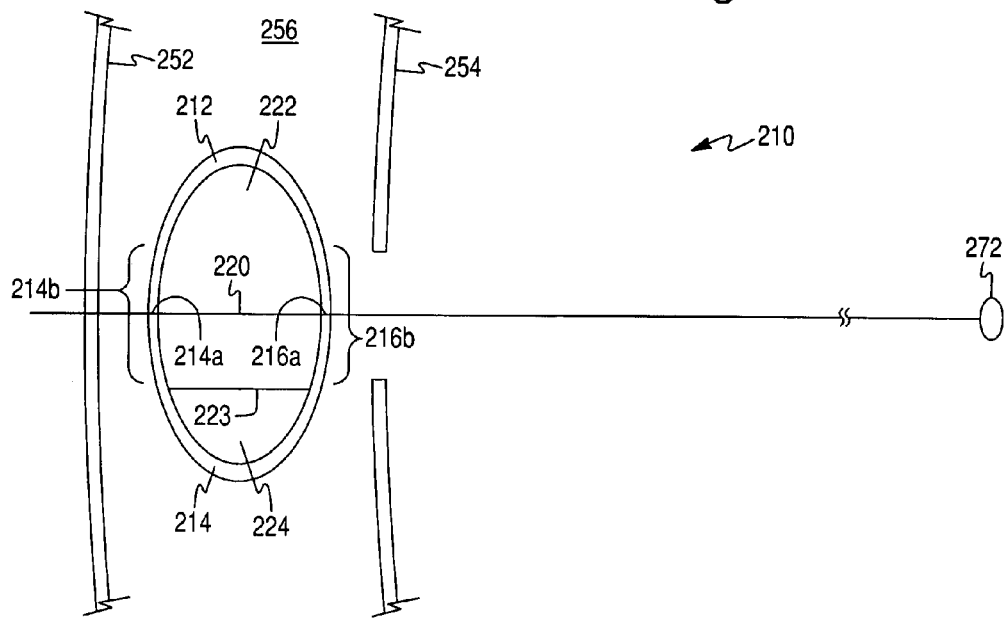
FIG. 9 is a schematic, enlarged view similar to FIG. 5, depicting the intraocular lens in the anterior chamber of the eye.
Figure 10:
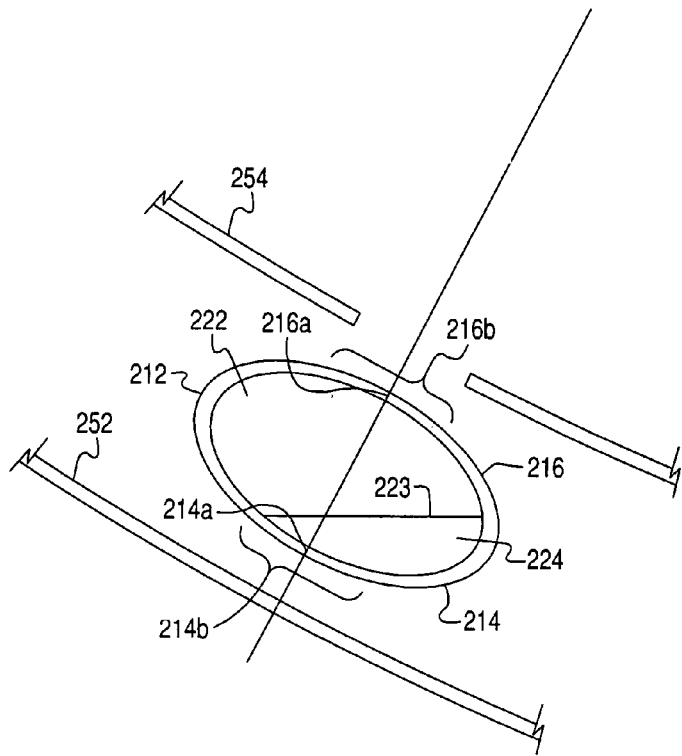
FIG. 10 is a schematic, enlarged view similar to FIG. 6, depicting the intraocular lens in the anterior chamber of the eye.

Although the intraocular lens of this second embodiment is illustrated in the posterior chamber 258 of the eye, it is to be understood that the lens 210 may be used in the anterior chamber 256, as shown in FIGS. 9 and 10. The intraocular lens in the anterior chamber may be the sole lens in the eye, or may supplement a physiological or synthetic lens placed in the posterior chamber 258. The intraocular lens may be placed in front of the iris, or between the iris and the capsular bag.

Figure 15:
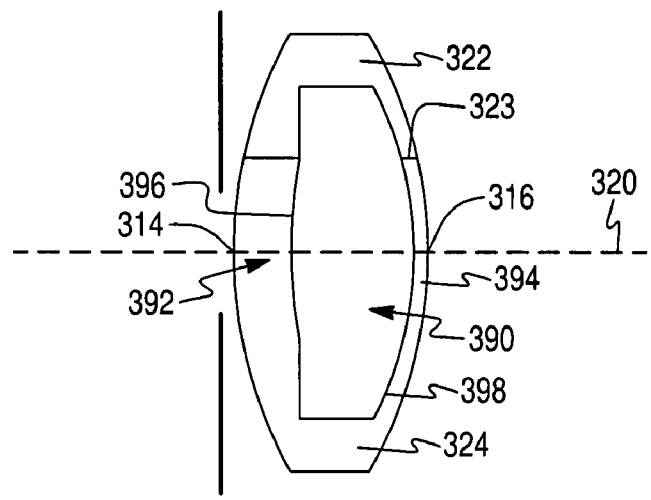
FIGS. 15 and 16 are schematic, enlarged views of an another embodiment of the intraocular lens in straight ahead and downward gazes, respectively.
Figure 16:
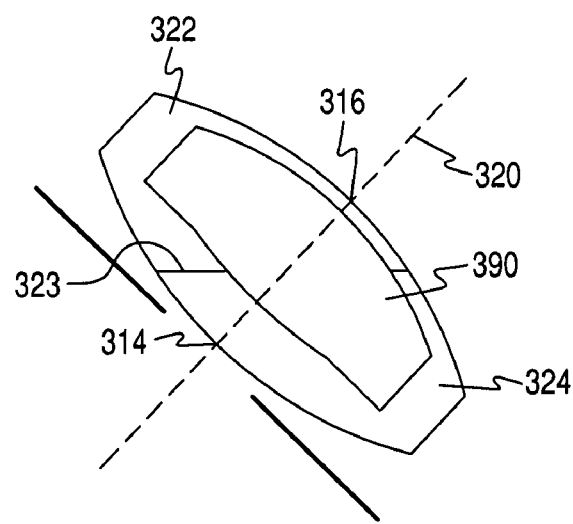

An example of a modification suitable for the first and second embodiments and falling within the scope of this invention is illustrated in FIGS. 15 and 16. In the interest of brevity and for the purpose of elaborating upon the structure, functions, and benefits of this modification, the description of the first and second embodiments is incorporated herein and not repeated in its entirety. In accordance with this modification, an intraocular lens 310 further comprises at least one supplemental internal lens element 390. The internal lens element 390 may be comprised of, for example, a flexible or rigid material, and may optionally include an internal chamber for holding a liquid or gas. The internal lens element 390 is retained, preferably in a fixed position, inside the intraocular lens body 312. By way of example and not necessarily limitation, webs or filaments may be used for suspending the internal lens element 390 in the fixed position. A first gap 392 is provided between the anterior surface 396 of the internal lens element 390 and the anterior wall 314. A second gap 394 is provided between the posterior surface 398 and the posterior wall 316. Upper fluid 322 and lower liquid 324 are allowed to flow through the gaps 392 and 394.

As shown in FIG. 15, the optically transmissive lower liquid 324 is present in a sufficient amount that orienting the optical axis 320 horizontally positions the optical axis 320 through the lower liquid 324. Most of the anterior visual zone and the posterior visual zone are immersed in the lower liquid 324. The optical axis 320 also passes through the internal lens element 390 in this modified embodiment. The contact interface 323 between the lower liquid 324 and the upper fluid 322 is above the optical axis 320, and preferably above the top edge of the internal lens element 390.

On the down gaze, the optical axis 320 of this modified embodiment is positioned at an angle relative to horizontal to translate the lower liquid 324 higher on the anterior wall 314 and lower on the posterior wall 316. The upper fluid 322 is present in the chamber 318 in a sufficient amount that, at any effective angle φ within a range, the upper fluid 322 translates down the posterior wall 316 until the optical axis 320 extends through the upper fluid 322 at the back vertex 216*a*. Preferably, at the range of effective angles, most of the surface area of the anterior visual zone is immersed in the lower liquid 324, and most of the posterior surface area of the posterior visual zone is immersed in the upper fluid 322.

Under these conditions, the light rays first travel through the lower liquid 324 before traveling through the upper fluid 322. However, in this modified embodiment the optical axis does not pass through the contact interface 323 of the upper fluid 322 and the lower liquid 324. Rather, the light passes through the internal lens element 390, thereby eliminating or substantially eliminating the contact interface 323 from the visual field. As a consequence, to the extent that a meniscus at the contact interface 123 and 223 of the first and second embodiments may contribute to glare or aberration, if any, the internal lens element 390 eliminates or substantially reduces the glare or aberration.

Examples of other modifications suitable for the first and second embodiments and falling within the scope of this invention are illustrated in FIGS. 17–28. In the interest of brevity and for the purpose of elaborating upon the structure, functions, and benefits of these modifications, the descriptions of the first and second embodiments and other modifications described above are incorporated herein and not repeated in their entireties.

In the first embodiment illustrated in FIGS. 1–4, when the eye is tilted upward by a sufficient angle, the upper fluid 122 may enter into the optically transmissive anterior visual zone 114*b* of the anterior wall 114, causing accommodation from far to near vision. In some instances this effect may be inconsequential or even desirable to the intraocular lens user, depending upon the preferences of the user. However, other intraocular lens users may wish to maintain accommodation for far vision at gazes upward of the horizontal orientation, to as high as φ=−90°, i.e., to vertical.

Figure 17:
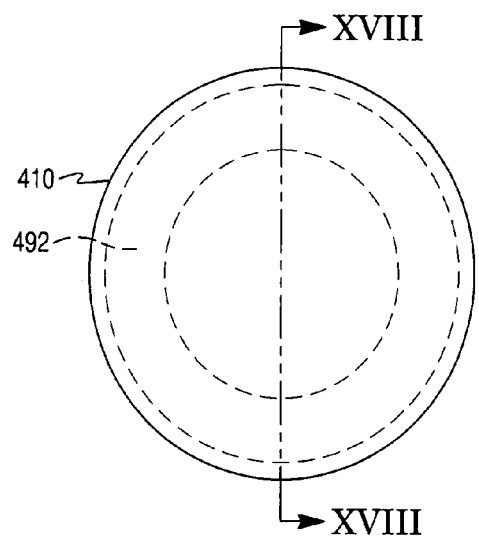
FIG. 17 is a front view of a modification to the intraocular lens of the first embodiment of the invention.
Figure 18:
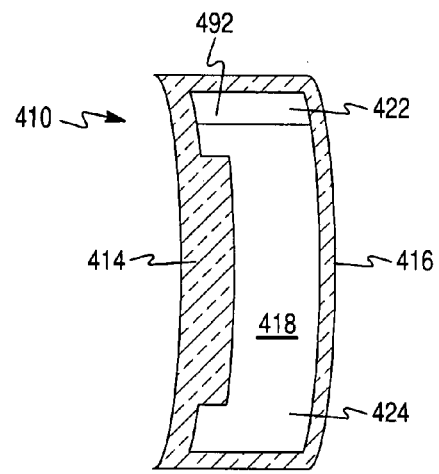
FIG. 18 is a side sectional view of FIG. 17.
Figure 19:
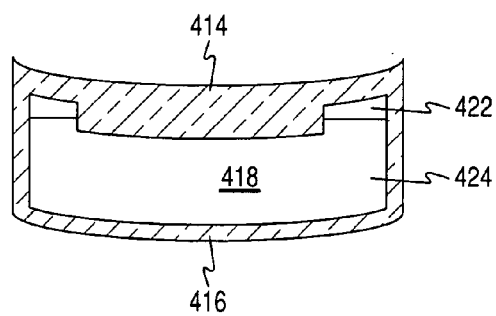
FIG. 19 is a side sectional view of FIG. 17, rotated by 90°.

In accordance with the modification illustrated in FIGS. 17–19, an intraocular lens 410 comprises an anterior wall 414, a posterior wall 416, and a chamber 418 between the anterior wall 414 and the posterior wall 416. The chamber 418 is preferably enclosed between the anterior wall 414 and the posterior wall 416, and more preferably is enclosed by a structure consisting of the anterior wall 414 and the posterior wall 416. The anterior wall 414 and posterior wall 416 are preferably spherical as shown in FIG. 17, although each may be aspheric, and may be modified into an aspheric shape or otherwise to compensate for astigmatism. The anterior wall 414 includes a dike comprising an annular channel or trench 492, which constitutes part of the chamber 418 and is formed in the anterior wall 414. In the illustrated embodiment, the channel 492 extends 360° around the perimeter of the anterior wall 414. It is to be understood that the channel 492 may extend only a portion of the way around the perimeter of the anterior wall 414, in which case the channel 492 is preferably arcuate. The chamber 418 includes an upper fluid 422 and a lower liquid 424. Preferably, the depth of the upper fluid 422 is smaller than the sectional height of the channel 492, as shown in FIG. 18. As the lens 410 is tilted upward into its vertical position shown in FIG. 19, the upper fluid 422 is maintained in the channel 492, out of the optical centers of the anterior and posterior walls 414 and 424. In this manner, the optical path to the retina passes through the lower liquid 424 while substantially avoiding the upper fluid 422.

Figure 20:
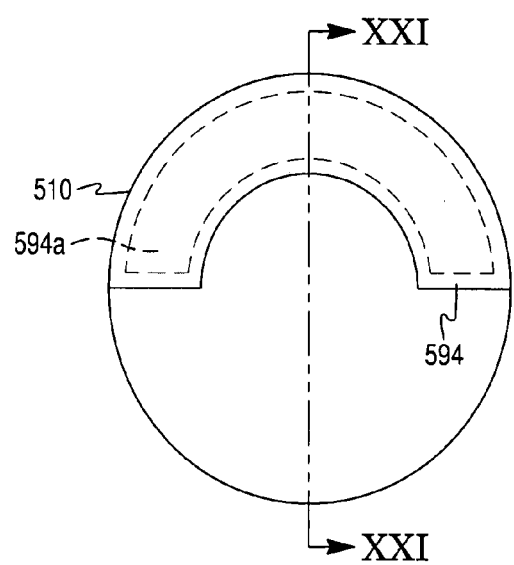
FIG. 20 is a front view of another modification to the intraocular lens of the first embodiment of the invention.
Figure 21:
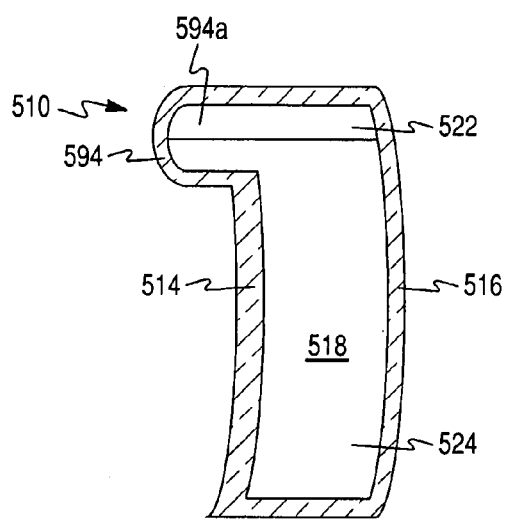
FIG. 21 is a side sectional view of FIG. 20.
Figure 22:
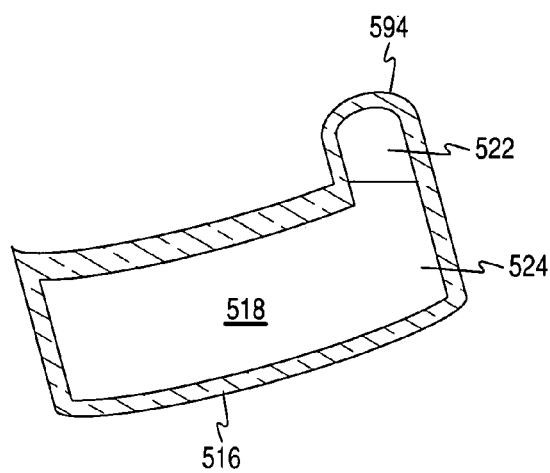
FIG. 22 is a side sectional view of FIG. 20, rotated by about 90°.

In accordance with the modification illustrated in FIGS. 20–22, an intraocular lens 510 comprises an anterior wall 514, a posterior wall 516, and a chamber 518 between the anterior wall 514 and the posterior wall 516. The chamber 518 is preferably enclosed between the anterior wall 514 and the posterior wall 516, and more preferably is enclosed by a structure consisting of the anterior wall 514 and the posterior wall 516. The anterior wall 514 and posterior wall 516 are preferably spherical as shown in FIG. 20, although each may be aspheric, and may be modified into an aspheric shape or otherwise to compensate for astigmatism. The anterior wall 514 includes a dike comprising a protuberance 594, which constitutes part of the anterior wall 514 and has a cavity 594a constituting part of the chamber 518. In the illustrated embodiment, the protuberance 594 is arcuate and extends about 180° around the perimeter of the anterior wall 514. It is to be understood that the protuberance 594 may extend around a small or greater portion or the entirety of the perimeter of the anterior wall 514. The chamber 518 includes an upper fluid 522 and a lower liquid 524. Preferably, the depth of the upper fluid 522 is smaller than the sectional height of the cavity 594a, as shown in FIG. 21. As the lens 510 is tilted upward towards its vertical position shown in FIG. 22, the upper fluid 522 is maintained in the cavity 594a of the protuberance 594, out of the optical zones of the anterior and posterior walls 514 and 524. In this manner, the optical path to the retina passes through the lower liquid 524 while substantially avoiding the upper fluid 522.

In the second embodiment illustrated in FIGS. 5 and 6, when the eye is tilted upward by a sufficient angle, the lower liquid 224 may enter into the optically transmissive anterior visual zone 216b of the posterior wall 216, causing accommodation from far to near vision. In some instances this effect may be inconsequential or even desirable to the intraocular lens user, depending upon the preferences of the user. However, some intraocular lens users may wish to maintain accommodation for far vision at gazes upward of the horizontal orientation, to as high as φ=−90°, i.e., to vertical.

Figure 23:
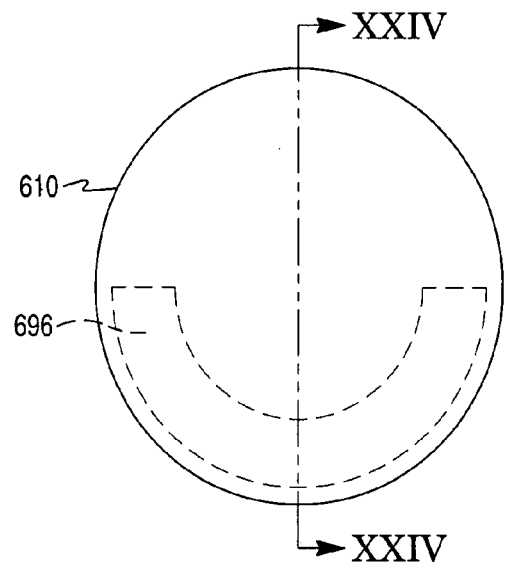
FIG. 23 is a front view of a modification to the intraocular lens of the second embodiment of the invention.
Figure 24:
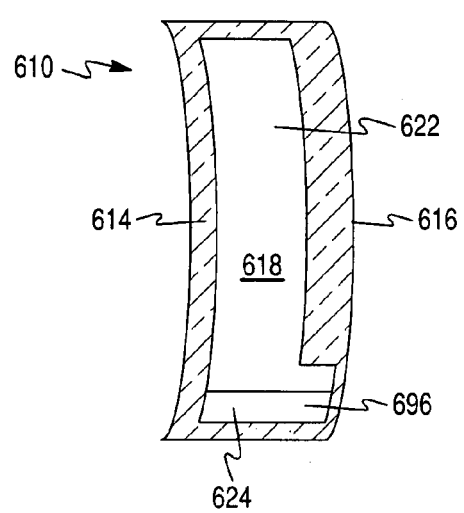
FIG. 24 is a side sectional view of FIG. 23.
Figure 25:
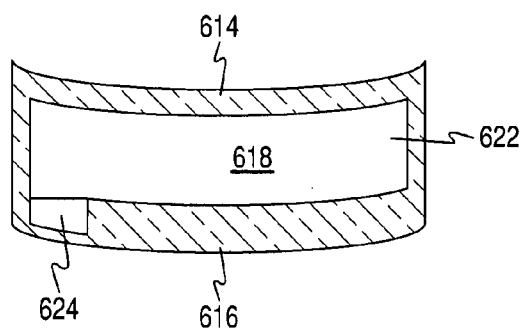
FIG. 25 is a side sectional view of FIG. 23, rotated by 90°.

In accordance with the modification illustrated in FIGS. 23–25, an intraocular lens 610 comprises an anterior wall 614, a posterior wall 616, and a chamber 618 between the anterior wall 614 and the posterior wall 616. The chamber 618 is preferably enclosed between the anterior wall 614 and the posterior wall 616, and more preferably is enclosed by a structure consisting of the anterior wall 614 and the posterior wall 616. The anterior wall 614 and posterior wall 616 are preferably spherical as shown in FIG. 23, although each may be aspheric, and may be modified into an aspheric shape or otherwise to compensate for astigmatism. The posterior wall 616 includes a dike comprising a channel or trench 696, which constitutes part of the chamber 618 and is formed in the posterior wall 616. In the illustrated embodiment, the channel 696 is arcuate and extends about 180° about the perimeter of the posterior wall 616. It is to be understood that the channel 696 may extend a greater or less portion or all of the way around the perimeter of the posterior wall 616. The chamber 618 includes an upper fluid 622 and a lower liquid 624. Preferably, the depth of the lower liquid 624 is smaller than the sectional height of the channel 696, as shown in FIG. 24. As the lens 610 is tilted upward into its vertical position shown in FIG. 25, the lower liquid 624 is maintained in the channel 696, out of the visual zones of the anterior and posterior walls 614 and 624. In this manner, the optical path to the retina passes through the upper fluid 622 while substantially avoiding the lower liquid 624.

Figure 26:
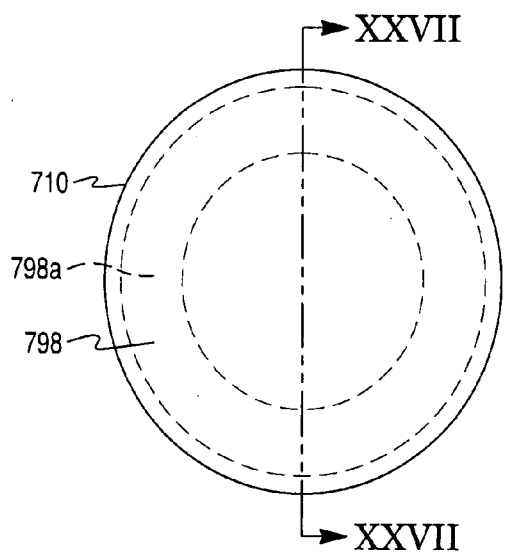
FIG. 26 is a front view of another modification to the intraocular lens of the second embodiment of the invention.
Figure 27:
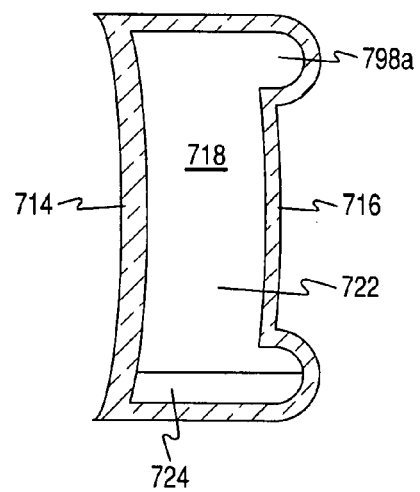
FIG. 27 is a side sectional view of FIG. 26.
Figure 28:
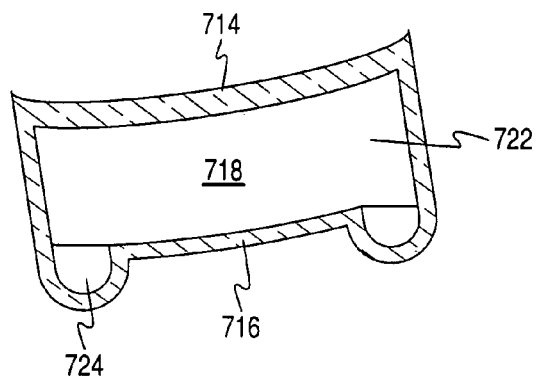
FIG. 28 is a side sectional view of FIG. 26, rotated by about 90°.

In accordance with the modification illustrated in FIGS. 26–28, an intraocular lens 710 comprises an anterior wall 714, a posterior wall 716, and a chamber 718 between the anterior wall 714 and the posterior wall 716. The chamber 718 is preferably enclosed between the anterior wall 714 and the posterior wall 716, and more preferably is enclosed by a structure consisting of the anterior wall 714 and the posterior wall 716. The anterior wall 714 and posterior wall 716 are preferably spherical as shown in FIG. 26, although each may be aspheric, and may be modified into an aspheric shape or otherwise to compensate for astigmatism. The posterior wall 716 includes a dike comprising an annular protuberance 798, which constitutes part of the posterior wall 716 and has an annular cavity 798a constituting part of the chamber 718. In the illustrated embodiment, the protuberance 798 extends about 360° around the perimeter of the posterior wall 716. It is to be understood that the protuberance 798 may extend a lesser degree around the perimeter of the posterior wall 716, in which case the protuberance is preferably arcuate. The chamber 718 includes an upper fluid 722 and a lower liquid 724. Preferably, the depth of the lower liquid 724 is smaller than the sectional height of the protuberance 798, as shown in FIG. 27. As the lens 710 is tilted to its vertical position shown in FIG. 28, the lower liquid 724 is maintained in the protuberance 798, out of the visual zones of the anterior and posterior walls 714 and 724. In this manner, the optical path to the retina passes through the upper fluid 722 while substantially avoiding the lower liquid 724.

Figure 29:
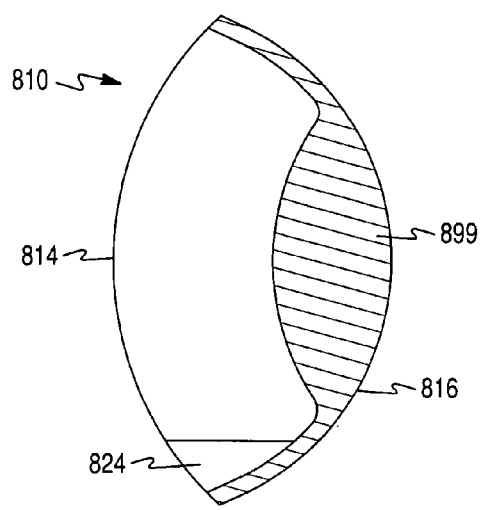
FIGS. 29 and 30 are each side sectional views according to additional modified embodiments of the invention.
Figure 30:
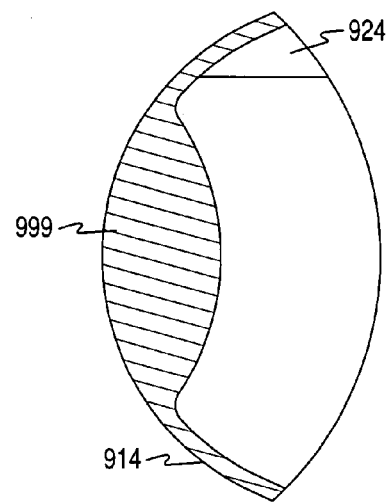

Other designs and configurations may also be practiced for channeling or displacing the secondary fluid away from the optical centers when the optic body is tilted upward relative to the horizontal position. For example and not necessarily limitation, the haptics may be provided with a channel that communicates with the lens chamber. Another example for displacing the secondary fluid away from the optical centers is shown in FIG. 29, in which an intraocular lens having a convex anterior wall 814 and a posterior wall 816 is provided. The posterior wall 816 has a concave outer surface (relative to the direction of light passing into the eye), and has a central bulb portion (or lens) 899 having a generally convex shape. The bulb portion 899 is preferably unitary with the posterior wall 816. As the intraocular lens 810 is tilted downward for reading or near vision, secondary liquid 824 will run forward towards the anterior optical center as described above in connection with the embodiments described above. On the other hand, as the intraocular lens 810 is tilted upward, the bulb portion 899 will direct the secondary liquid 824 towards the bulb edges, away from the posterior optical center. FIG. 30 illustrates a similar embodiment functioning on the same basic principals, except that the bulb portion 999 is part of the anterior wall 914 and the secondary fluid 924 is the upper fluid.

Methods of making optic bodies are well known in the intraocular lens art and are described throughout the literature. These methods, which are suitable for use with the various aspects of the present invention, include, not necessarily by limitation, molding and lathing, with injection molding being perhaps the most commonly employed and well known of these methods. The formation of a molded body with an internal chamber is well known in the injection molding and lathing arts. Methods of gel-capsule manufacture as applied in the pharmaceutical industry may also be applied, as these methods describe introduction of fluids into capsules without leaving vacuum or air space within the capsule. As mentioned above, the anterior and posterior walls may be made as a unitary piece, or separately then joined together, such as by adhesive, fusion, or the like.

The optic body and optional internal lens element 390 preferably comprise a material or materials biologically compatible with the human eye, and capable of injection molding, lathing, or the like. In particular, the materials are preferably non-toxic, non-hemolytic, and non-irritant. The optic body preferably is made of a material that will undergo little or no degradation in optical performance over its period of use. Unlike a contact lens, however, the material does not have to be gas permeable, although it may be. For example, the optic body may be constructed of rigid biocompatible materials, such as, for example, polymethylmethacrylate, or flexible, deformable materials, such as silicones, deformable acrylic polymeric materials, hydrogels and the like which enable the lens body to be rolled, deformed, or folded for insertion through a small incision into the eye. The above list is merely representative, not exhaustive, of the possible materials that may be used in this invention. For example, collagen or collagen-like materials, e.g., collagen polymerized with a monomer or monomers, may be used to form the optic body. However, it is preferred to make the lens body of a material or materials, e.g., elastic, adapted for folding or deformation to facilitate insertion of the intraocular lens into the eye.

The lens surface may be modified with heparin or any other type of surface modification designed to increase biocompatibility and decrease possibility of capsular haze occurring.

The intraocular lens of this invention may include haptics, which are generally shown in FIGS. 1 and 2, in which the haptics are designated by reference numeral 190. Haptics generally serve to anchor the optics body in place in the eye. Haptics are usually attached directly to the lens body. Various types of haptics are well known in the art, and their incorporation into this invention would be within the purview of an ordinary artisan having reference to this disclosure. Generally, the typical haptic is a flexible strand of nonbiodegradable material fixed to the lens body. By way of example, suitable haptics for this invention may be made of one or more materials known in the art, including polypropylene, poly(methyl methacrylate), and any biocompatible plastic or material in use now or in the future that are used to hold the lens in place. The haptics used with invention may possess any shape or construction adapted or adaptable for use with this invention for securing the lens body in place in the eye. In the posterior chamber, the haptics secure the optical lens within the capsular bag, whereas in the anterior chamber haptics may extend into the area defined between the anterior iris and posterior cornea. For anterior chamber intraocular lenses, it is also within the scope of this invention to use an "iris claw", which hooks onto the fibers of the iris.

The upper fluid and the lower liquid may be introduced and retained in the body chamber prior to implanting the IOL into a human eye. The upper and lower fluids may be introduced into the chamber by any technique consistent with the objects of this invention. For example, a syringe of the like may be used for injecting the upper fluid and lower liquid into the chamber. Optionally, an entry port may be provided in the optic body for introducing the upper fluid and lower liquid into the chamber of the optic body. The entry port may be formed during injection molding, by penetrating through one or both of the walls with a suitable hole-making instrument, such as a drill or pin, or it may established by the injecting instrument, e.g., syringe, during introduction of the fluids. The location of the entry port is not critical, i.e., the entry port may be in the anterior wall, posterior wall, or the interface between the walls. Other techniques may also be used to form the optic body.

It is within the scope of the method of this invention to provide the optic body with a vent port for expelling gas (usually air) inside the optic body chamber as the upper fluid and lower liquid are introduced through the entry port. The vent may be separate from the entry port, or may consist of the entry port such that gas entrapped in the chamber is expelled through the entry port as the upper and lower fluids are introduced into the chamber. Alternatively, the chamber may be evacuated prior to the introduction of the upper fluid and the lower liquid. Subsequent to introducing the upper fluid and lower liquid into the chamber, the entry port and optional vent may be sealed to enclose the chamber in a known manner, such as by fusion or plugging with a compatible material, which may be the same or different than the material from which the optical body is comprised.

It is within the scope of this invention, however, the insert the IOL body into the human eye, then to subsequently inject a portion or all of the upper fluid and the lower liquid into the implanted IOL body in situ. The benefit to this latter variation is that an IOL body that is not filled with fluids/liquids is more amenable to folding and deformation.

Both upper fluid and the lower liquid are preferably optically transmissive, and it is a preferred embodiment that when emulsified by shaking or position change minimal mixing of the upper fluid and the lower liquid occurs, and whatever mixing does occur quickly separates out again. The substantially immiscible upper fluid and lower liquids are preferably optically transparent. It is within the scope of the invention for one or more of the optically transmissive fluids to possess a tint of any color that is not dense enough to significantly impede the transmission of light or the intended objects of this invention. Although the upper fluid is preferably a liquid, it is within the scope of this invention for the upper fluid to be in the form of a gas or vacuum.

This invention is not limited to the use of only two fluids/liquids in the intraocular lens. Three or more fluids of different refractive indexes can be used to create a multipower, multifocus lens so that objects between far (pr) and near (pp) can be focused upon more clearly. Tri-focals of this invention preferably have three liquids of different densities, with the refractive index of the fluids decreasing with fluid density.

Fluids that may be used for in the lens body include, but are not limited to, those common to ophthalmic surgery, such as the following: water, aqueous humor, hyaluron, viscoelastics, polydimethyl siloxane, bis-phenyl propyl dimethicone, phenyl tri-methicone, di-phenyl-di-methyl siloxane copolymer (vinyl-terminated), cyclopentasiloxane, phenyl trimethicone, polydimethyl methyl phenyl siloxane, polymethyl phenyl siloxane, liquid chitosan, heparin, perfluoro-n-octane (perfluoron), perfluoroperhydrophenanthrene, perfluoromethyldecalin, perfluoropentane, perfluoro-1,3-dimethyl cyclohexane, perfluorodecalin, perfluoroperhydro-p-fluorene, and glycerine. It is preferable, but not necessary, that one of the fluids used in the intraocular lens of this invention is water, such as distilled water, to save cost and hazards of broken or ruptured intraocular lenses in vivo.

Many other fluorocarbon liquids may be selected for use as the lower liquid, the upper fluid, or the lower liquid and upper fluid. Representative fluorocarbon fluids that may be used for providing the desired refractive properties of this invention include haloalkanes. Representative haloalkanes that may be useful include trichloromonofluoromethane, dichlorodifluoromethane, monochlorotrifluoromethane, bromotrifluoromethane, dichloromonofluoromethane, monochlorodifluoromethane, dichlorotetrafluoroethane. Other fluorocarbons include 2,2,2-trifluoroethanol, octofluoropentanol-1, dodecafluoroheptanol-1. Other liquids include methanol, acetonitrile, ethyl ether, acetone, ethanol, methyl acetate, propionitrile, 2,2 dimethyl butane, isopropyl ether, 2-methyl pentane, ethyl acetate, acetic acid, D-mannitol, and D-sorbitol.

Many polymethyl/silicon liquid species can be used, including, by way of example, the following: tetrachlorophenylsilsesquixane-dimethyl siloxane copolymer, poly (methylsilsesquioxane, 100% methyl), poly(methylhydridosilsesquioxane, 90%), poly(phenylsilsesquioxane), 100% phenyl, poly(phenyl-methylsilsesquioxane 90% phenyl 10% methyl), dimethicone copolyol PPG-3 oleyl ether (aka alkyl polyether), hydroxymethyl acetomonium PG dimethicone (aka betaine), amino propyl dimethicone (aka amine).

It is within the scope of this invention to select two or more different liquids or fluids as the upper fluid, and to select two or more different liquids as the lower liquid. Dilution of miscible liquids of different indices of refraction may be effective for tailoring the refractive index of the upper fluid or lower liquid phase. Additionally, the dilution of salts, sugars, etc. into the liquids may modify the refractive index. Examples of aqueous salts include sodium chloride, calcium chloride, zinc chloride, potassium chloride, and sodium nitrate (referred to herein as "NaN"). Generally, the concentration of the salts and sugars should be no higher than their saturation points.

These represent chemicals that may be safe within the eye. Other chemicals that are not safe, i.e., biologically compatible with the eye, are less desirable but can have the same visual outcome if maintained within the optical cavity and not exposed to the ocular media within the eye.

As described in connection with the first embodiment above, the intraocular lens can be inserted into the posterior chamber of the human eye, preferably into the capsular bag posterior to the iris to replace the physiological (natural) lens in the capsular bag positioned using known equipment and techniques. Posterior implantation is preferred because, among other reasons, this is the location from which the physiological lens is removed. By way of example, intracapsular cataract extraction and IOL implantation utilizing clear corneal incision ("CCI"), phacoemulsification or similar technique may be used to insert the intraocular lens after the physiological crystalline lens has been removed from the capsular bag. The incision into the eye may be made by diamond blade, a metal blade, a light source, such as a laser, or other suitable instrument. The incision may be made at any appropriate position, including along the cornea or sclera. It is possible to make the incision "on axis", as may be desired in the case of astigmatism. Benefits to making the incision under the upper lid include reduction in the amount of stitching, cosmetic appeal, and reduced recovery time for wound healing. The intraocular lens is preferably rolled or folded prior to insertion into the eye, and may be inserted through a small incision, such as on the order of about 3 mm. It is to be understood that as referred to in the context of this invention, the term "capsular bag" includes a capsular bag having its front surface open, torn, partially removed, or completely removed due to surgical procedure, e.g., for removing the physiological lens, or other reasons. For example, in FIGS. 1 and 2 the capsular bag 160 has an elastic posterior capsule, and an anterior capsular remnant or rim defining an opening through which the physiological lens was removed.

Alternatively, the intraocular lens may be inserted in the anterior chamber between the cornea and the iris. In an anterior chamber implant, the intraocular lens is generally situated forward of, or mounted to, the iris.

When light rays pass between non-opaque media, there is a mathematical description of how light is bent, or refracted. This is termed Snell's Law and is based on the Index of Refraction ("IR") of the medium. Different non-opaque media have their own specific index of refraction, and mixed media take on their own individual index of refraction. If two media are placed in contact with one another but do not mix, light will be refracted as it travels from the first medium into the second medium. If a third medium is provided, the light will be refracted again as it passes between the second and third media.

Intraocular lenses according to this invention may be used for various eye conditions and diseases, including, for example, aphakia, pseudophakia, anterior cortical cataract extraction (acce), posterior cortical cataract extraction (pcce), accommodative restorative surgery for presbyopes, treatment of retinal degenerative diseases (i.e., low vision), in refractive correction surgery, and the like. In the case of retinal degenerative diseases, the device preferably may be used to maximize the retinal area used for sufferers of macular degeneration, i.e. minimizing the area affected by scotoma (or minimizing the blinding effect of the scotoma by imaging away from it).

Figure 31:
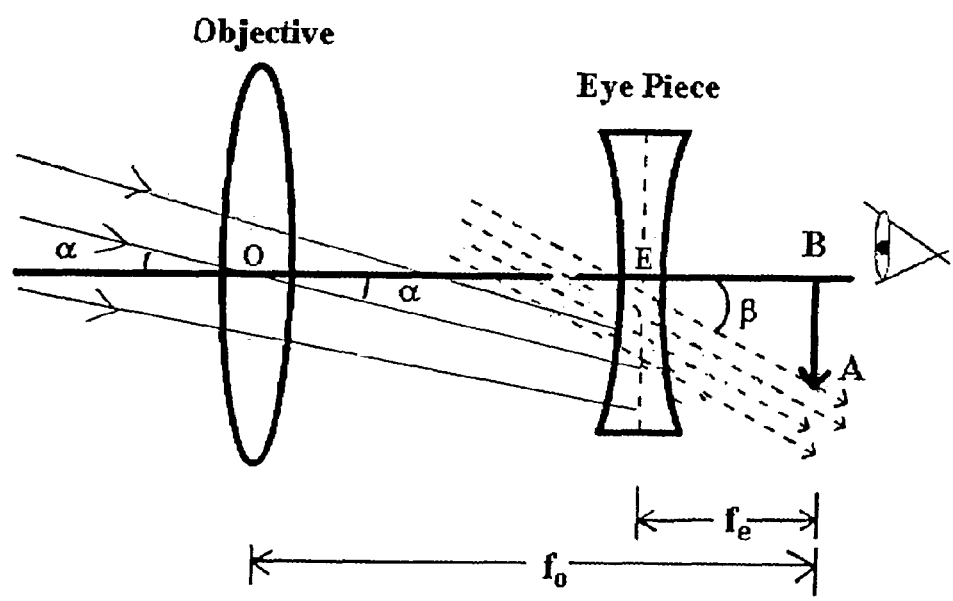
FIG. 31 shows an example of a Galilean telescopic system.

Intraocular lenses according to the present invention can be used as the ocular lens of a Galilean or Keplerian type device to provide a telescopic benefit and a near-magnifying benefit. These benefits are particularly useful in the treatment of retinal degenerative diseases. The telescopic benefit is derived from the effective power of the ocular lens in straight-ahead gaze being calculated to be negative in power. With a negative ocular lens, the user may put a positive objective lens in front of the ocular lens. The positive objective lens may comprise, for example, an eyeglass lens, contact lens, and/or an implant in front of our ocular lens. Preferably, the focal points of the objective and ocular lenses are coincident with one another, as is the case in a Galilean telescope. The combination of the negative ocular (intraocular) lens and the positive objective lens creates a telescopic power of a Galilean type, as shown in FIG. 31. As referred to herein and generally understood in the art, a "negative power" lens is a "diverging lens," i.e., a lens having a cumulative effect of diverging light passing through the lens. On the other hand, a "positive power" lens is a "converging lens," i.e., a lens having a cumulative effect of converging light rays passing through the lens.

The fluids and lens curvatures are chosen to effect the desired magnification change on down gaze needed to magnify around a near scotoma. Generally this will involve both the objective and ocular lenses in total providing additional plus power in down gaze (compared to straight ahead gaze). Thus, the lenses together provide a Galilean distance telescope in straight-ahead gaze. Further, the ocular lens, alone or in combination with the objective lens, provides a near point low vision magnifier in down gaze.

A person with macular degeneration generally requires from about 1.5× to about 5.0× magnification. The higher the magnification, the smaller the user's field of view and, therefore, a balance must be reached. Preferably, this balance is dictated by the patient's pupil size, and in particular, maximizing the field of view for the particular pupil size. The greater amount of the papillary area the ocular lens can fill without introducing an opaque housing into the papillary line of sight, the better the field of view and the magnified image will appear to the user. Determination of suitable ocular and objective lenses for a particular magnification is within the purview of those skilled in the art. Generally, the focal length of the objective divided by the focal length of the eyepiece equals the magnifying power of the telescope.

Another aspect of this invention comprises the treatment of one or more residual refractive disorders of the eye after the eye has received an element that allows it to focus, e.g., an intraocular lens, a scleral expansion device, or other element that is designed to substitute for or increase the function of the human accommodative system. Treatment of residual refractive disorder after implantation with IOL or other implement that allows for restoration of focus may be achieved by mechanically or chemically altering a structure of the eye, such as the cornea. Representative treatment techniques include, but are not necessarily limited to, light or laser refractive surgery of the cornea (including PRK [photo-refractive keratectomy], LASIK [laser intra-stromal keratectomy], LASEK [laser epithelial keratectomy]) performed with excimer lasers, YAG (yttrium-aluminum-garnet) lasers or other ablative lasers of single frequency or frequency modulation including but not limited to frequency doubling or tripling, thermal keratoplasty, conductive keratoplasty including radio waves, corneal ring segments. Each of these techniques on a human eye having a natural lens is well known and the art and described in various literature documents too numerous to list. One example of a literature document describing techniques for shaping the cornea is U.S. Pat. No. 4,994,058. Application of these techniques on a human eye containing a corrective element, such as an intraocular lens, may be performed by those of ordinary skill in the refractive correction arts without undue experimentation.

EXAMPLES

All examples were modeled on the Zemax Version 10.0 optical design program, SE edition, from Focus Software, Inc.

The human eye was first modeled as a typical or schematic adult human emmetrope, as described in the Optical Society of America Handbook. Each of the models described below is for a posterior chamber IOL design. The following assumptions were made for the human eye for the purposes of the calculations. The model was assumed to have spherical surfaces only (whereas the real cornea and lens are actually aspherics). Each structure of the schematic human eye was assumed to be made of a material having a uniform or homogenous index (whereas in the real human eye, the index of refraction may vary somewhat through each structure of the eye). The model also assumed that the capsular bag walls were very thin and parallel, i.e., non-existent. The lens was assumed to have symmetric radius, i.e., spherical. The pr was assumed to be 10 meters. Three wavelengths with equal weighting were used for optimization and evaluation: 510 nm, 560 nm, and 610 nm to provide a simple approximation of the human photopic response.

Walker, Bruce H., Optical Design for visual Systems, SPIE Press (2000). The Abbe wavelength dispersion is assumed to be 55.0 for all natural materials. The indices at other wavelengths were calculated based on $n_D$ and the dispersion value. Modeling was performed for small pupil sizes of 1.5 mm. The initial values assumed for the eye are listed below in Table 1.

TABLE 1

| Surface | Radius (mm) | Thickness (mm) | Refr. Index (@589 nm) | Material |
|---|---|---|---|---|
| Anterior Cornea | 7.80 | 0.55 | 1.3771 | Cornea |
| Posterior Cornea | 6.50 | 3.05 | 1.3374 | Aqueous Humor |
| Anterior Lens | 10.20 *20.83** | 4.00 | 1.4200 | Natural lens |
| Posterior Lens | −6.00 *−4.26** | 16.6 *16.80** | 1.3360 | Vitreous Humor |
| Retina | *−12.67** | | | |

*italics indicates values optimized through Zemax program, under assumed conditions as listed.

The above assumptions and conditions were maintained for the IOL designs, with the natural lens replaced by the IOL. The overall length of the eye models was kept constant. The IOL thickness was allowed to adjust during optimization, but not to exceed 4.0 mm.

Figure 12:
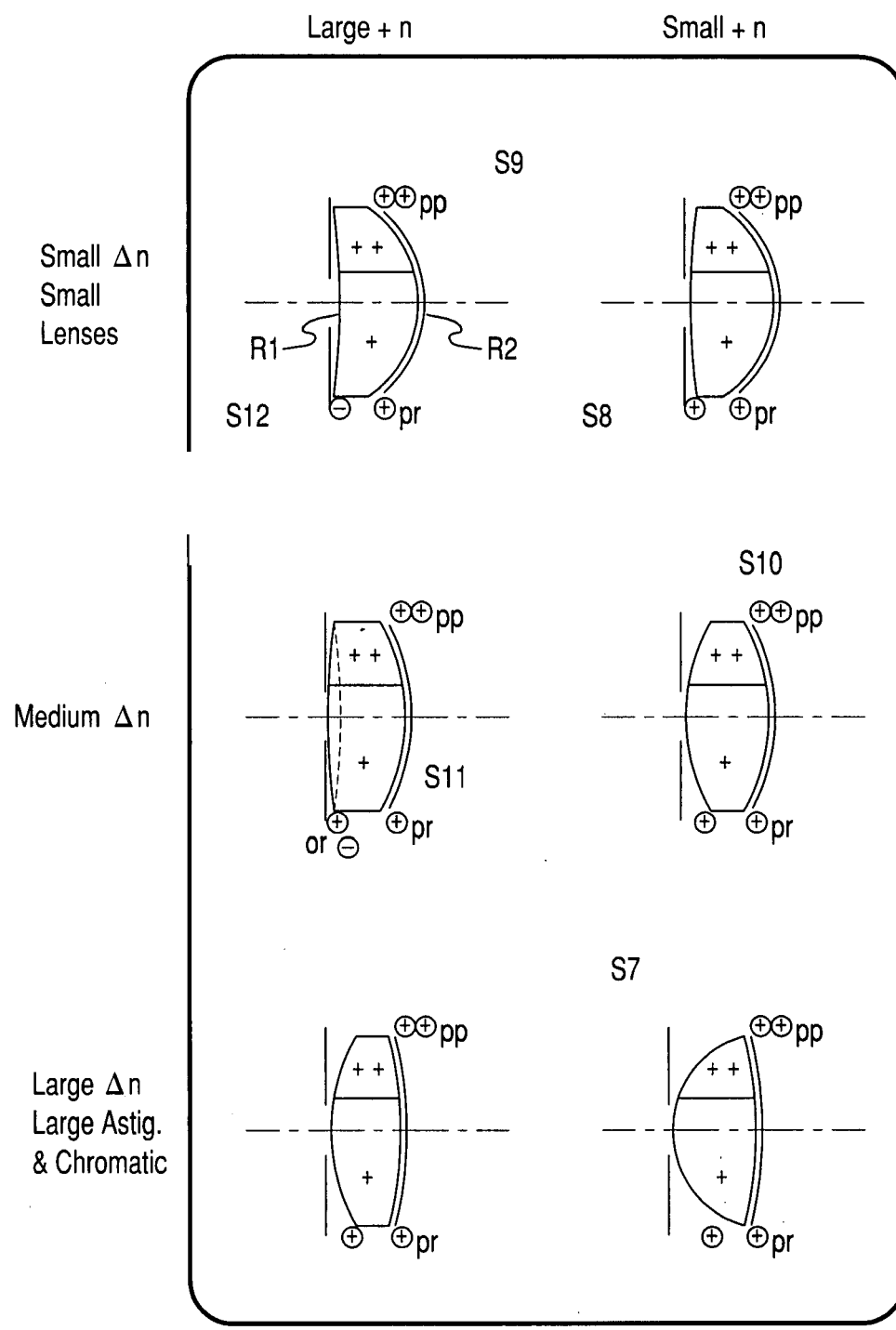
FIGS. 12–14 represent IOL schematics for the examples presented below.

According to one set of preferred IOL designs illustrated in FIG. 12, the lower liquid is the primary liquid and has a lesser refractive index than the upper liquid. Accordingly, in this preferred embodiment the upper liquid has a greater refractive index and imparts accommodative power (+ power) on down gaze by increasing the effective power of the posterior IOL surface. Models were made for the combinations of fluids in Table 2. The index of refraction value were either taken as reported in the literature at 37° C. (body temperature) in a saturated solution, or were estimated based on calculations using three (3) wavelengths (of 510 nm, 560 nm, and 610 nm).

TABLE 2

| Label | Lower Liquid | Upper Liquid | $n_D1$** | $n_D2$** | R1*** | R2*** | Thickness**** |
|---|---|---|---|---|---|---|---|
| S9 | Aq-NaN | PDMS- (37° C.) | 1.38543 | 1.39908 | −43.750 | −2.52 | 2.12 |
| S8 | Aq-NaCl | PDMS (37° C.) | 1.37794 | 1.39908 | 6.081 | −3.65 | 2.32 |
| S12 | Aq-CaCl | Mineral Oil | 1.44287 | 1.46408 | −14.770 | −3.98 | 1.62 |
| S10 | Aq-KCl | PDMS- (37° C.) | 1.36035 | 1.39908 | 1.875 | −6.82 | 1.58 |
| S11 | Aq-ZnCl | Mineral Oil | 1.40229 | 1.46408 | 5.837 | −9.00 | 3.54 |
| S7 | Aq-NaCl | Mineral Oil | 1.37789 | 1.46408 | 3.029 | −14.00 | 2.30 |

**$n_D1$ and $n_D2$ are refractive index of lower liquid and the upper liquid, respectively, at or about its saturation limit at 589 nm wavelength.
***R1 and R2 are the radius of curvature of the anterior surface and the posterior surface, respectively, in millimeters.
****Lens thickness was measured in millimeters.

The shapes of the anterior and posterior walls were calculated for hypothetical cases by modifying the adult human emmetrope model to simulate an IOL. The crystalline lens material was replaced with the lower fluid to simulate horizontal pr gaze (at 10 m), and the pp (250 mm) was modeled in a directly vertical 90° downward gaze angle using two liquids with the interface perpendicular to the optical axis. The posterior radius of the lens was selected to obtain the needed change of power with the upper liquid introduced to accommodate for pp (at about 250 mm). Other assumptions listed above for the model eye were also made. Gaze angles of less than 90° were then evaluated without re-optimizing the model parameters. Specifically, gaze angles of 50° and 70° were investigated. The 90°, 70°, and 50° gaze angles were each evaluated at the following five field points of 0°, ±7.5°, and ±15°. The root mean square (RMS) of each spot radius value was then recorded. Reported below are the averages of the five field values, and the RMS for the on-axis (0°) field point. All RMS values are in microns.

TABLE 3

| Label | RMS Spot: Average of 5 Fields | | | RMS Spot: On-Axis Value | | |
|---|---|---|---|---|---|---|
| | 90° | 70° | 50° | 90° | 70° | 50° |
| S9 | 4.81 | 5.14 | 7.26 | 3.87 | 4.47 | 6.97 |
| S8 | 4.78 | 4.89 | 7.93 | 3.21 | 4.00 | 8.16 |
| S12 | 4.03 | 4.03 | 5.94 | 2.88 | 3.11 | 5.31 |
| S10 | 9.28 | 9.45 | 15.59 | 5.16 | 6.84 | 15.71 |
| S11 | 5.41 | 6.164 | 17.95 | 3.45 | 5.86 | 18.99 |
| S7 | 7.29 | 8.79 | 26.29 | 4.53 | 8.37 | 27.67 |

Smaller RMS values generally indicate less aberration and better focus on the retina. Generally, values less than 7.00 microns are preferred for the assumed conditions.

The IOL schematics are laid out as though plotted on a chart, with the actual fluid's refractive index along the horizontal axis (abscissa) and the difference in the index values of the two fluids on the vertical axis (ordinate). Internal to the lens schematics, the fluids are labeled with the following symbols:

+ a liquid having an index of refraction greater than the humors in which the IOL is immersed when implanted;

++ a liquid having an index of refraction greater than the humors and the adjacent "+" liquid;

− a liquid having an index of refraction lower than the humors;

−− a liquid having an index of refraction lower than the humors and the adjacent "−" liquid.

The cornea (not shown) is to the left of the IOL schematics, and the iris is shown immediately to the left of the IOL schematics. The surface that produces the optical power change (pr to pp adaption) is shown with a double line.

As shown in FIG. 12, the IOL schematics for this embodiment preferably had concave/concave, convex/concave walls, or flat/concave walls. Fluid combinations S9 and S10 were less preferred due to the steep curvatures of R1 (anterior surface) or R2 (posterior surface).

Figure 13:
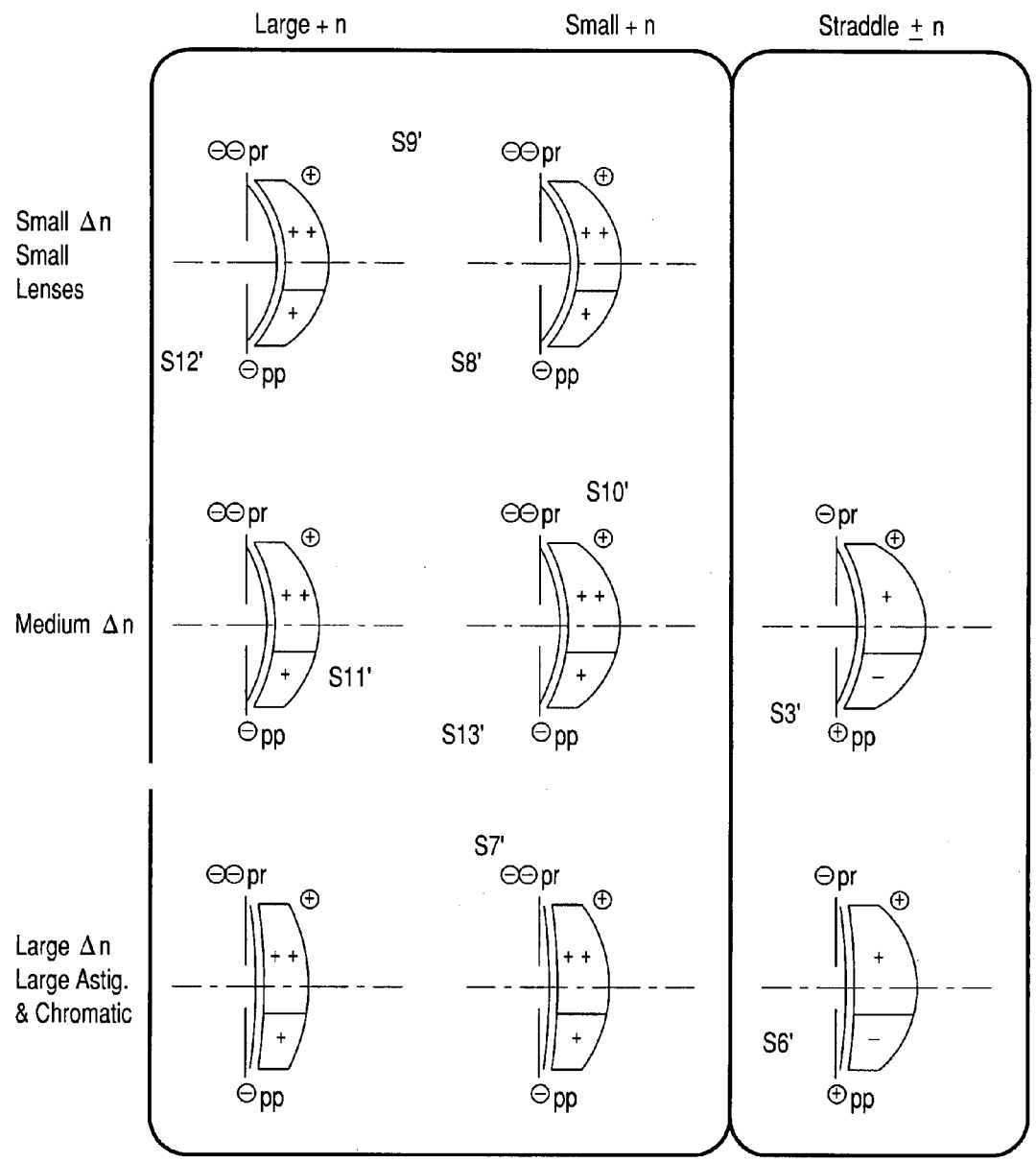

According to another set of preferred IOL designs illustrated in FIG. 13, the upper liquid is the primary liquid and has a greater refractive index than the lower liquid. Hence, the lower liquid imparts accommodative power (+ power) on down gaze by increasing the effective power of the lens. Models were made for the following combinations of fluids:

TABLE 4

| Label | Lower Liquid | Upper Liquid | $n_D1$ | $n_D2$ | R1 | R2 |
|---|---|---|---|---|---|---|
| S9' | PDMS- (37° C.) | Aq-NaN | 1.39908 | 1.38543 | −2.90 | −1.703 |
| S8' | PDMS (37° C.) | Aq-NaCl | 1.39908 | 1.37794 | −4.40 | −2.032 |
| S12' | Mineral Oil | Aq-CaCl | 1.46408 | 1.44287 | −4.45 | −2.770 |
| S10' | PDMS- (37° C.) | Aq-KCl | 1.39908 | 1.36035 | −8.10 | −2.458 |
| S11' | Mineral Oil | Aq-ZnCl | 1.46408 | 1.40229 | −12.95 | −4.296 |
| S13' | Mineral Oil | Aq-NaN | 1.46408 | 1.38543 | −16.50 | −4.564 |
| S7' | Mineral Oil | Aq-NaCl | 1.46408 | 1.37789 | −18.17 | −4.661 |
| S5' | PDMS (37° C.) | Water (37° C.) | 1.39908 | 1.33100 | −14.35 | −2.760 |
| S6' | Mineral oil | Water (37° C.) | 1.46408 | 1.33100 | −28.40 | −5.032 |

The shapes of the anterior and posterior walls were calculated for hypothetical cases by modifying the adult human emmetrope model to simulate an IOL. The crystalline lens material was replaced with the upper fluid to simulate horizontal pr gaze (at 10 m), and the pp (at about 250 mm) was modeled in a directly vertical 90° downward gaze angle using two fluids with the interface perpendicular to the optical axis. The anterior radius of the lens was selected to obtain the needed change of power with the lower liquid introduced to accommodate for pp. Again, assumptions made above for the model eye were applied, as needed. Gaze angles of less than 90° were then evaluated without re-optimizing the model parameters.

TABLE 5

| Label | RMS Spot: Average of 5 Fields | | | RMS Spot: On-Axis Value | | |
|---|---|---|---|---|---|---|
| | 90° | 70° | 50° | 90° | 70° | 50° |
| S8' | 7.06 | 7.17 | 8.61 | 6.23 | 6.38 | 7.77 |
| S12' | 5.88 | 5.91 | 6.55 | 4.56 | 4.69 | 5.55 |
| S10' | 5.24 | 5.54 | 10.67 | 4.23 | 4.82 | 10.20 |
| S11' | 4.03 | 4.73 | 13.33 | 2.73 | 3.92 | 12.78 |
| S13' | 3.94 | 5.18 | 17.23 | 2.58 | 4.40 | 16.47 |
| S7' | 3.97 | 5.59 | 13.60 | 2.63 | 4.87 | 18.25 |
| S5' | 4.66 | 5.80 | 17.64 | 3.54 | 5.26 | 17.10 |
| S6' | 4.11 | 8.39 | 31.63 | 2.68 | 7.74 | 30.06 |

As shown in FIG. 13, the IOL schematics for these examples preferably had concave/concave walls, with the anterior surface concavity more pronounced than in FIG. 12. Fluid combinations S5', S8', S9', S10', and S12' were less preferred due to the small sizes of the IOL R1 and/or R2.

Figure 14:
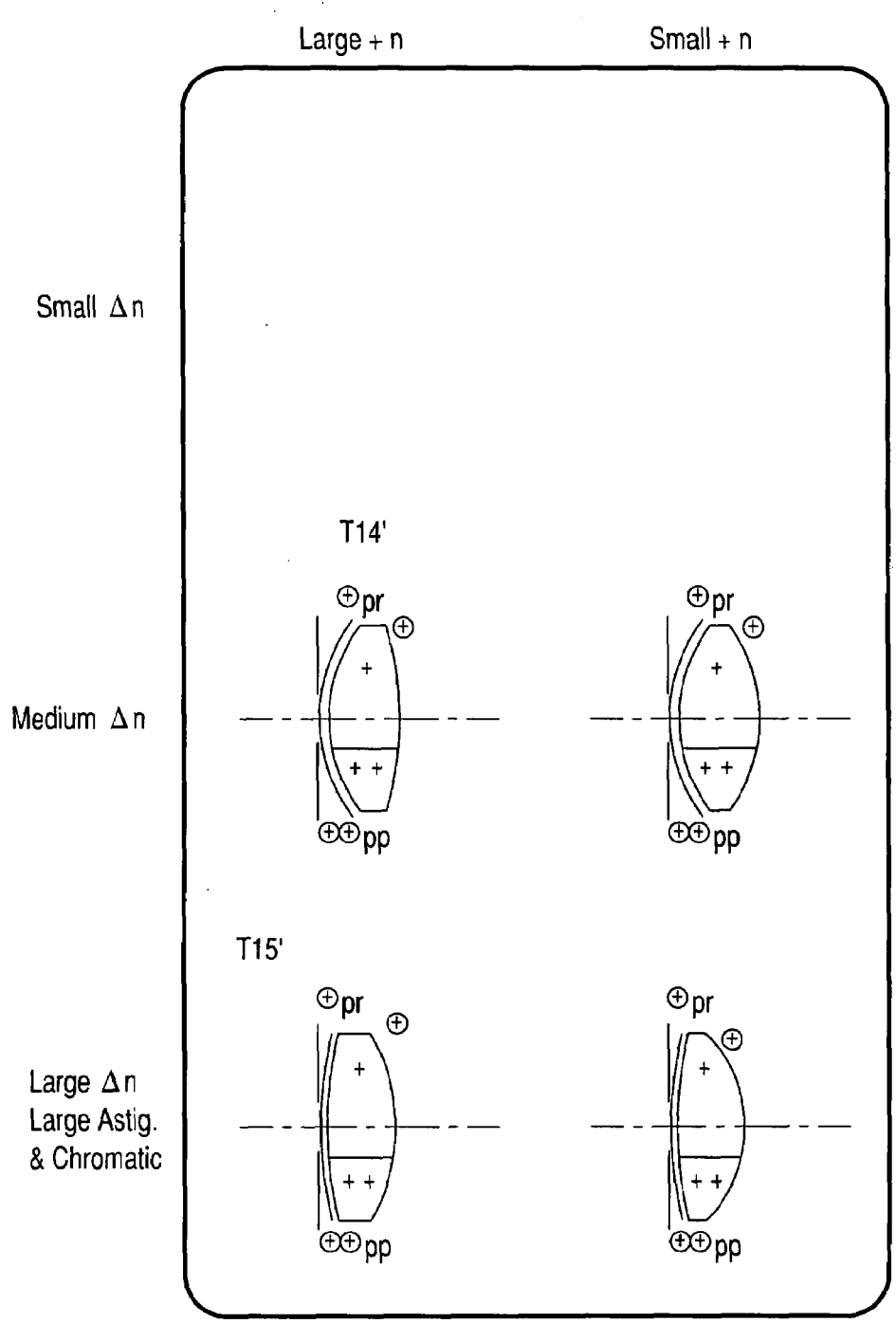

According to another set of preferred IOL designs illustrated in FIG. 14, the upper liquid is the primary liquid and has a smaller refractive index than the lower liquid. Models were made for the combinations of fluids set forth in Table 6, with the corresponding results reported in Table 7:

TABLE 6

| Label | Lower Liquid | Upper Liquid | nD1 | nD2 | R1 | R2 |
|---|---|---|---|---|---|---|
| T14' | PDMS- (37° C.) | Aq-CaCl | 1.39908 | 1.44287 | 9.19 | −4.750 |
| T15' | PDMS (37° C.) | Glycerol | 1.39908 | 1.47238 | 15.30 | −4.022 |

TABLE 7

| | RMS Spot: Average of 5 Fields | | | RMS Spot: On-Axis Value | | |
|---|---|---|---|---|---|---|
| Label | 90° | 70° | 50° | 90° | 70° | 50° |
| T14' | 5.14 | 7.31 | 19.56 | 3.34 | 4.43 | 14.81 |
| T15' | 4.65 | 8.29 | 28.38 | 3.04 | 5.24 | 23.17 |

Convex/concave wall structures were preferred for these examples.

It was observed from modeling that the tilt of the fluid interface (downward gazes not equal to 90°) may cause astigmatism and chromatic aberrations; which can be minimized by decreasing the differential value between the fluid indices. However, too small an index differential may require compensation vis-à-vis reduction to the radii of curvature. Reduction in radii of curvature may produce IOLS have diameters that are too small and increased spherical aberration and coma. Thus, a fundamental tradeoff exists between the normal aberrations (no tilt of the fluids) and the performance as the gaze departs from directly downward.

The lens schematics illustrated in the accompanying drawings are intended to show general trends, and are not intended or shown as precise designs. The illustrated schematics are also not intended to be exhaustive of the scope of possible IOL body designs within the scope of this invention.

The foregoing detailed description of the preferred embodiments of the invention has been provided for the purposes of illustration and description, and is not intended to be exhaustive or to limit the invention to the precise embodiments disclosed. The embodiments were chosen and described in order to best explain the principles of the invention and its practical application, thereby enabling others skilled in the art to understand the invention for various embodiments and with various modifications as are suited to the particular use contemplated. It is intended that the scope of the invention cover various modifications and equivalents included within the spirit and scope of the appended claims.

What is claimed is:

1. An intraocular lens for a human eye, the intraocular lens comprising:
   an optic body sized and configured to be received in the human eye, the optic body comprising an anterior wall with an anterior optical center, a posterior wall with a posterior optical center, and a chamber between the anterior wall and the posterior wall, the optic body having an optical axis intersecting the anterior wall at the anterior optical center and the posterior wall at the posterior optical center;
   an optically transmissive primary fluid having a first density and a first refractive index, the primary fluid being contained in the chamber of the optic body in a sufficient amount that orienting the optical axis in a horizontal orientation for far vision positions the optical axis through the primary fluid and immerses the anterior and posterior optical centers in the primary fluid; and
   an optically transmissive secondary fluid substantially immiscible with the primary fluid and having a second density and a second refractive index that are different than the first density and the first refractive index, the secondary fluid contained in the chamber of the optic body in a sufficient amount that orienting the optical axis for near vision at a range of effective downward angles relative to the horizontal orientation positions the optical axis to extend through the primary fluid and the secondary fluid,
   wherein the chamber further comprises a dike for inhibiting flow of the secondary fluid to the anterior and posterior optical centers when the optic body is oriented to angle the optical axis upward relative to the horizontal orientation; and
   wherein the range of effective downward angles comprises an angle of 90 degrees relative to the horizontal orientation, wherein at the angle of 90 degrees the optical axis extends through the primary fluid and the secondary fluid.

2. An intraocular lens according to claim 1, wherein the dike is sufficient in capacity to prevent the secondary fluid from reaching the anterior and posterior optical centers when the optic body is oriented to place the optical axis upward and perpendicular to the horizontal orientation.

3. An intraocular lens according to claim 2, wherein the dike comprises a channel formed in a member selected from the group consisting of the anterior wall and the posterior wall.

4. An intraocular lens according to claim 3, wherein the channel is arcuate.

5. An intraocular lens according to claim 3, wherein the channel is annular.

6. An intraocular lens according to claim 1, wherein the dike comprises a protuberance formed in a member selected from the group consisting of the anterior wall and the posterior wall.

7. An intraocular lens according to claim 6, wherein the protuberance is arcuate.

8. An intraocular lens according to claim 6, wherein the protuberance is annular.

9. An intraocular lens according to claim 1, wherein at the angle of 90 degrees the optical axis extends through a fluid interface where the primary and secondary fluids contact one another.

10. An intraocular lens according to claim 1, wherein the first density is greater than the second density, and wherein orienting the optical axis at the range of effective downward angles translates the primary fluid toward the anterior wall and positions the optical axis to extend through the primary fluid at the anterior optical center and the secondary fluid at the posterior optical center.

11. An intraocular lens according to claim 1 wherein the second density is greater than the first density, and wherein orienting the optical axis at the range of effective downward angles translates the secondary fluid toward the anterior wall and positions the optical axis to extend through the secondary fluid at the anterior optical center and the primary fluid at the posterior optical center.

12. An intraocular lens according to claim 1, wherein one of the fluids is a gas.

13. An intraocular lens according to claim 12, wherein the gas comprises air.

* * * * *